US005827800A

United States Patent [19]

Förster et al.

[11] Patent Number: 5,827,800

[45] **Date of Patent: *Oct. 27, 1998**

[54] ALKYL SULPHINYL AND ALKYL SULPHONYL-1,2,4-THIADIAZOLYLOXY ACETAMIDES AND THEIR USE AS HERBICIDES

[75] Inventors: Heinz Förster, Kadenbach; Hans-Joachim Santel; Markus Dollinger, both of Leverkusen, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 732,239

[22] PCT Filed: Apr. 19, 1995

[86] PCT No.: PCT/EP95/01472

§ 371 Date: Oct. 25, 1996

§ 102(e) Date: Oct. 25, 1996

[87] PCT Pub. No.: WO95/29990

PCT Pub. Date: Nov. 9, 1995

[30] Foreign Application Priority Data

May 2, 1994 [DE] Germany .......................... 44 15 338.4

[51] Int. Cl.$^6$ ........................ C07D 285/08; A01N 43/836

[52] U.S. Cl. ........................... 504/262; 548/129; 548/130

[58] Field of Search .................................... 548/130, 129; 504/262

[56] References Cited

U.S. PATENT DOCUMENTS

| | | | |
|---|---|---|---|
| 4,645,525 | 2/1987 | Forster | 71/88 |
| 5,090,991 | 2/1992 | Forster | 71/90 |

*Primary Examiner*—Robert Gerstl
*Attorney, Agent, or Firm*—Sprung Kramer Schaefer & Briscoe

[57] ABSTRACT

The invention relates to novel alkyl sulphinyl and alkyl sulphonyl-1,2,4-thiadiazolyloxy acetamides of formula (I)

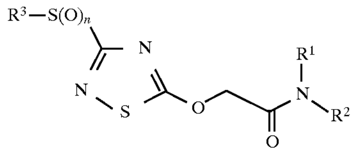

(I)

in which n is the numbers 1 or 2, $R^1$ is hydrogen or possibly substituted alkyl, alkenyl, alkinyl or aralkyl, $R^2$ is possibly substituted alkyl, alkenyl, alkinyl, cycloalkyl, cycloalkenyl, aralkyl, aryl, alkoxy, alkenyloxy or alkinyloxy, or $R^1$ and $R^2$ together with the nitrogen atom to which they are bound form a possibly substituted, saturated or unsaturated nitrogen heterocycle which may contain other hetero atoms and to which a benzo group may be annellated, and $R^3$ is possibly substituted alkyl, aryl or arylalkyl, and also processes and novel intermediate products for producing the novel compounds and their use as herbicides.

6 Claims, No Drawings

ALKYL SULPHINYL AND ALKYL SULPHONYL-1,2,4-THIADIAZOLYLOXY ACETAMIDES AND THEIR USE AS HERBICIDES

The invention relates to novel alkylsulphinyl- and alkylsulphonyl-1,2,4-thiadiazolyloxyacetamides, to processes and novel intermediates for their preparation and to their use as herbicides.

It has already been disclosed that certain alkylsulphinyl- and alkylsulphonyl-1,2,4-thiadiazolyloxyacetamides, for example N-isopropyl-α-(3-methylsulphinyl-1,2,4-thiadiazol-5-yl-oxy)-acetanilide, exhibit herbicidal properties (cf., for example, EP-A 348 737 and the preceding, but not prepublished, Patent Application German Patent Specification 4 317 323 of 25.5.1993). However, the activity of these previously disclosed compounds is not completely satisfactory in all areas of application, particularly at low application rates and concentrations.

The novel alkylsulphinyl- and alkylsulphonyl-1,2,4-thiaazolyloxyacetamides of the general formula (I) have now been found,

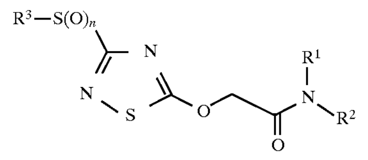
(I)

in which n represents the numbers 1 or 2, $R^1$ represents hydrogen or represents alkyl, alkenyl, alkinyl or aralkyl which are in each case optionally substituted, $R^2$ represents alkyl, alkenyl, alkinyl, cycloalkyl, cycloalkenyl, aralkyl, aryl, alkoxy, alkenyloxy or alkinyloxy which are in each case optionally substituted, or $R^1$ and $R^2$, together with the nitrogen atom to which they are bonded, form an optionally substituted, saturated or unsaturated nitrogen heterocycle which can contain additional heteroatoms and to which a benzo grouping can be fused, and $R^3$ represents alkyl, aryl or arylalkyl which are in each case optionally substituted, where the compounds N-isopropyl-α-(3-methylsulphinyl-1,2,4-thiadiazol-5-yl-oxy)-acetanilide, N-isopropyl-α-(3-methylsulphonyl-1,2,4-thiadiazol-5-yl-oxy)-acetanilide, N-isopropyl-α-(3-ethylsulphinyl-1,2,4-thiadiazol-5-yl-oxy)-acetanilide, N-iso-propyl-α-(3 -ethylsulphonyl-1,2,4-thiadiazol-5-yl-oxy)-acetanilide, N-isopropyl-α-(3-propylsulphinyl-1,2,4-thiadiazol-5-yl-oxy)-acetanilide, N-isopropyl-α-(3-propylsulphonyl-1,2,4-thiadiazol-5-yl-oxy)-acetanilide—cf. EP-A 348 737—and also the compounds N-methyl-N-(4-fluoro-phenyl)-α-(3-methylsulphinyl-1,2,4-thiadiazol-5-yl-oxy)-acetamide,N-methyl-N-(4-fluoro-phenyl)-α-(3-methylsulphonyl-1,2,4-thiadiazol-5-yl-oxy)-acetamide,N-methyl-N-(4-fluoro-phenyl)-α-(3-ethylsulphonyl-1,2,4-thiadiazol-5-yl-oxy)-acetamide,N-ethyl-N-(4-fluoro-phenyl)-α-(3-methylsulphinyl-1,2,4-thiadiazol-5-yl-oxy)-acetamide,N-ethyl-N-(4-fluoro-phenyl)-α-(3-methylsulphonyl-1,2,4-thiadiazol-5-yl-oxy)-acetamide and N-ethyl-N-(4-fluoro-phenyl)-α-(3-ethylsulphonyl-1,2,4-thiadiazol-5-yl-oxy)-acetamide—cf. German Patent Specification 4 317 323 of 25.5.1993—are excepted by disclaimer.

In addition, it has been found that the novel alkylsulphinyl- and alkylsulphonyl-1,2,4-thiadiazolyloxyacetamides of the general formula (I) are obtained if (a) 1,2,4-thiadiazole derivatives of the general formula (II)

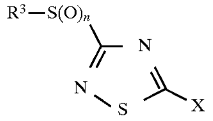
(II)

in which x represents halogen or the grouping —$S(O)_n$—$R^3$, and n and $R^3$ have the abovementioned meaning, are reacted with hydroxyacetamides of the general formula (III)

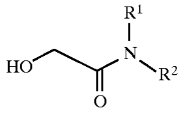
(III)

in which $R^1$ and $R^2$ have the abovementioned meaning, where appropriate in the presence of a diluent, where appropriate in the presence of an acid-binding agent and where appropriate in the presence of a catalyst, or if (b) alkyl(aryl-, aralkyl-)thio-1,2,4-thiadiazolyloxyacetamides of the general formula (IV)

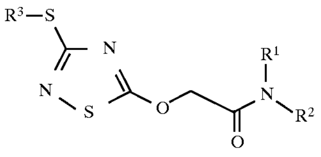
(IV)

in which $R^1$, $R^2$ and $R^3$ have the abovementioned meaning, are reacted with an oxidizing agent, where appropriate in the presence of a catalyst and where appropriate in the presence of a diluent.

Finally, it has been found that the novel alkylsulphinyl- and alkylsulphonyl-1,2,4-thiadiazolyloxyacetamides of the general formula (I) possess interesting herbicidal properties.

While in some cases exhibiting very good tolerability with regard to cultivated plants, for example cotton, the novel compounds of the formula (I) surprisngly exhibit a substantially more powerful effect against weeds which are difficult to control than does the chemically similar, known compound N-isopropyl-α-(3-methylsulphinyl-1,2,4-thiadiazol-5-yl-oxy)-acetanilide.

The invention preferably relates to compounds of the formula (I) in which n represents the numbers 1 or 2, $R^1$ represents hydrogen or $C_1$–$C_8$-alkyl (which is optionally substituted by fluorine, chlorine, cyano or $C_1$–$C_4$-alkoxy), represents $C_2$–$C_8$-alkenyl (which is optionally substituted by fluorine and/or chlorine), represents $C_2$–$C_8$-alkinyl or represents benzyl, $R^2$ represents $C_1$–$C_8$-alkyl (which is optionally substituted by fluorine, chlorine, cyano or $C_1$–$C_4$-alkoxy), or $C_2$–$C_8$-alkenyl (which is optionally substituted by fluorine and/or chlorine), represents $C_2$–$C_8$-alkinyl, represents $C_3$–$C_6$-cycloalkyl (which is optionally substituted by chlorine and/or $C_1$–$C_3$-alkyl), represents $C_5$-or $C_6$-cycloalkenyl, represents benzyl (which is optionally substituted by fluorine, chlorine and/or $C_1$–$C_4$-alkyl), represents phenyl (which is optionally substituted by fluorine, chlorine, bromine, iodine, cyano, nitro, $C_1$–$C_4$-alkyl, trifluoromethyl, $C_1$–$C_4$-alkoxy and/or $C_1$–$C_4$-alkylthio), represents $C_1$–$C_8$-alkoxy (which is optionally substituted by $C_1$–$C_4$-alkoxy), or represents $C_3$–$C_4$-alkenyloxy, or $R^1$ and $R^2$, together with the nitrogen atom to which they are bonded, form a saturated or unsaturated, five- to seven-membered nitrogen heterocycle which is optionally substituted once to three times by $C_1$–$C_3$-alkyl and which is optionally benzo fused, and $R^3$ represents $C_1$–$C_8$-alkyl (which is optionally substituted by fluorine, chlorine, bromine, cyano, $C_1$–$C_4$-alkoxy, dioxolanyl or dioxanyl) or represents phenyl or phenyl-$C_1$–$C_2$-alkyl (which are in each case optionally substituted by fluorine, chlorine, bromine, cyano, nitro, $C_1$–$C_4$-alkyl or $C_1$–$C_4$-alkoxy), with the exception of the compounds which are excepted above by disclaimer.

The invention relates, in particular, to compounds of the formula (I) in which n represents the numbers 1 or 2, $R^1$ represents methyl, ethyl, n- or i-propyl, n-, i- or s-butyl, or n-, i- or s-pentyl (which are in each case optionally substituted by fluorine, chlorine, cyano, methoxy or ethoxy), or represents propenyl, butenyl, propinyl or butinyl, $R^2$ represents methyl, ethyl, n- or i-propyl, n-, i or s-butyl, n-, i- or s-pentyl, or n-, i- or s-hexyl (which are in each case optionally substituted by fluorine, chlorine, cyano, methoxy or ethoxy), represents propenyl, butenyl, pentenyl, propinyl, butinyl or pentinyl, represents cyclopentyl or cyclohexyl (which are in each case optionally substituted by methyl and/or ethyl), represents cyclohexenyl, represents benzyl (which is optionally substituted by fluorine, chlorine and/or methyl) or represents phenyl (which is in each case optionally substituted by fluorine, chlorine, bromine, cyano, nitro, methyl, ethyl, trifluoromethyl, methoxy or ethoxy), or represents methoxy, ethoxy, n- or i-propoxy, n-, i- or s-butoxy, or n-, i- or s-pentyloxy (which are in each case optionally substituted by methoxy or ethoxy), or $R^1$ and $R^2$, together with the nitrogen atom to which they are bonded, represent piperidinyl which is optionally substituted one to three times by methyl and/or ethyl, represent pyrrolidinyl which is optionally substituted once or twice by methyl and/or ethyl, represent perhydroazepinyl or represent 1,2,3,4-tetrahydro(iso)-quinolinyl, and $R^3$ represents methyl, ethyl, n- or i-propyl, n-, i-, s- or t-butyl, n-, i-, s- or t-pentyl (which are in each case optionally substituted by fluorine, chlorine, cyano, methoxy or ethoxy) or represents phenyl or benzyl (which are in each case optionally substituted by fluorine, chlorine, cyano, methyl or methoxy), with the exception of the compounds which are excepted above by disclaimer.

Examples of the possible meanings of the grouping

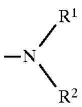

in the formula (I) are listed in the following Table 1.

TABLE 1

Examples of the meaning of the grouping

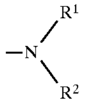

| 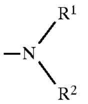 | 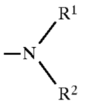 |
|---|---|
| $-N(CH_3)_2$<br>$-N(C_2H_5)_2$<br>$-N(C_3H_7)_2$ | $-N(C_4H_9)_2$<br>$-N(CH_2CH{=}CH_2)_2$<br>$-N(CH_2C{\equiv}CH)_2$ |
| 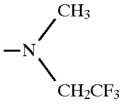 | 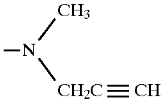 |
| 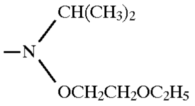 | 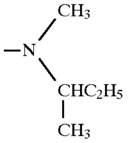 |
| 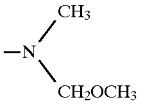 | 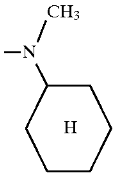 |
| 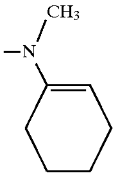 | 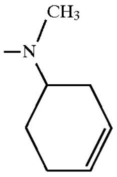 |
| 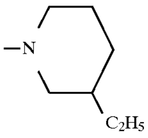 | 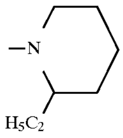 |
| 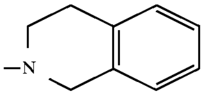 | 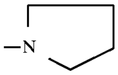 |
| 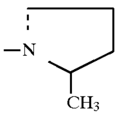 | 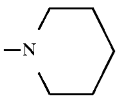 |
| 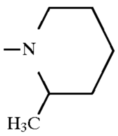 | 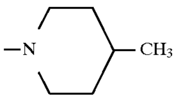 |

TABLE 1-continued
Examples of the meaning of the grouping
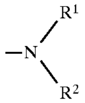
| 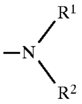 | 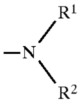 |
|---|---|
| 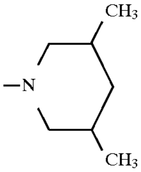 | 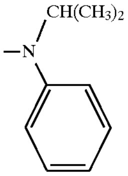 |
| 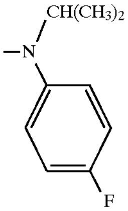 | 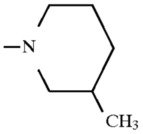 |
| 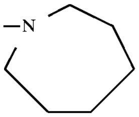 | 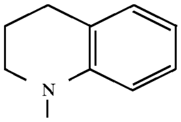 |
| 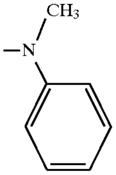 | 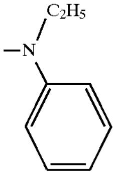 |
| 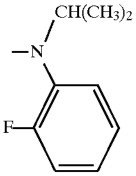 | 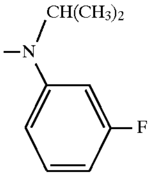 |
| 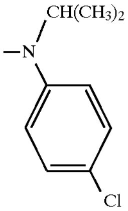 | 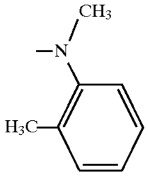 |
| 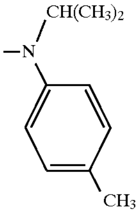 | 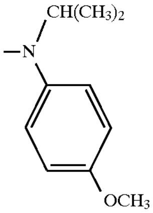 |
TABLE 1-continued
Examples of the meaning of the grouping
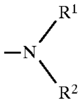
| 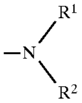 | 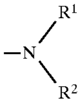 |
|---|---|
| 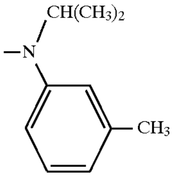 | 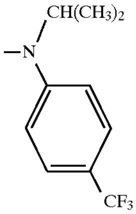 |
| 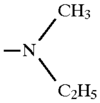 | 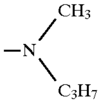 |
| 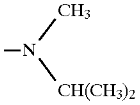 | 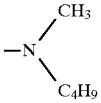 |
| 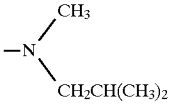 | 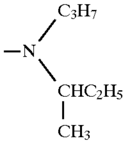 |
| 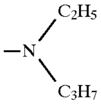 | 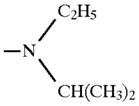 |
| 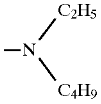 | 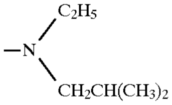 |
| 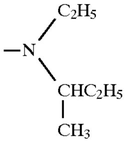 | 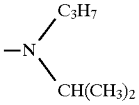 |
| 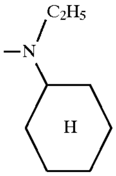 | 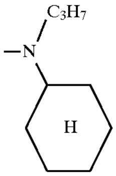 |

TABLE 1-continued
Examples of the meaning of the grouping
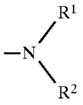
| 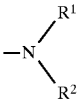 | 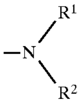 |
|---|---|
| 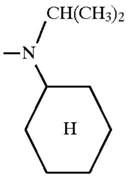 | 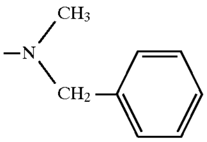 |
| 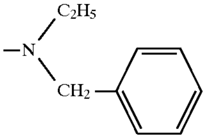 | 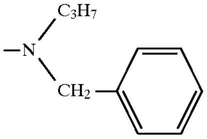 |
| 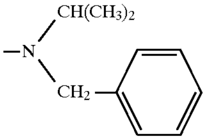 | 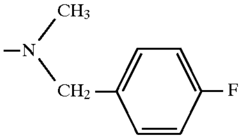 |
| 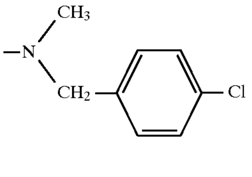 | 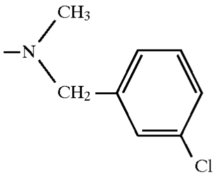 |
| 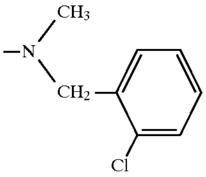 | 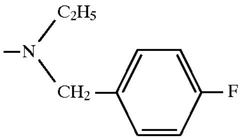 |
| 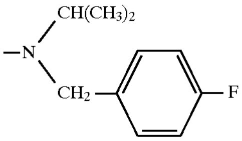 | 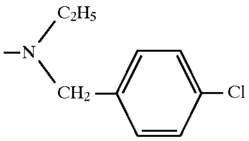 |
| 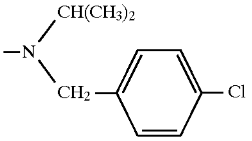 | 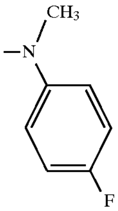 |
TABLE 1-continued
Examples of the meaning of the grouping
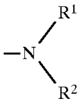
| 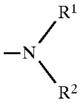 | 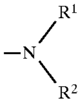 |
|---|---|
| 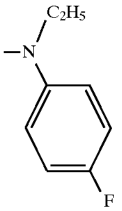 | 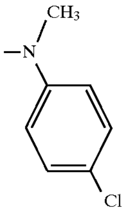 |
| 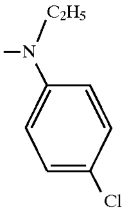 | 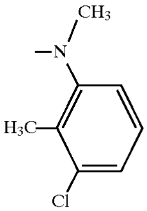 |
| 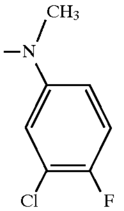 | 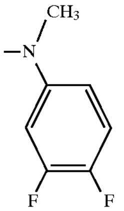 |
| 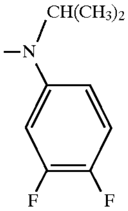 | 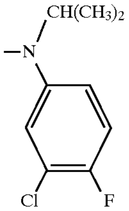 |
| 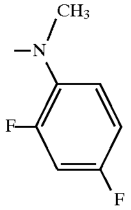 | 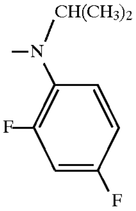 |
| 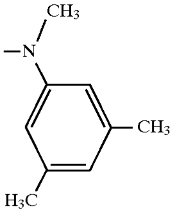 | 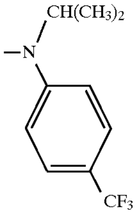 |

TABLE 1-continued

Examples of the meaning of the grouping

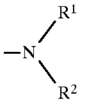

| 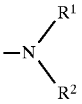 | 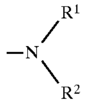 |
|---|---|
| 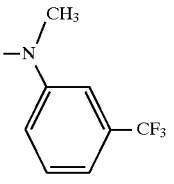 | 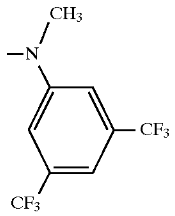 |
| 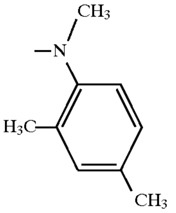 | 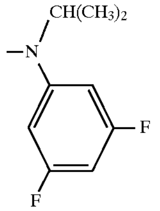 |
| 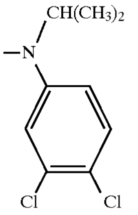 | 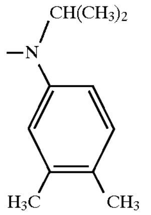 |
| 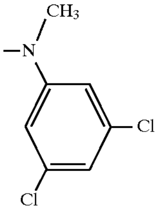 | 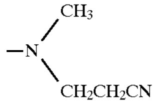 |
| 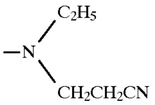 | $-N(CH_2CH_2CN)_2$ |
| 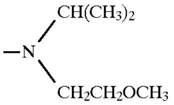 | 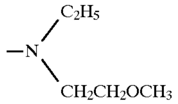 |
| 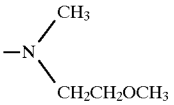 | 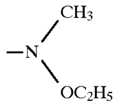 |
| 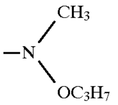 | 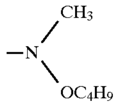 |

TABLE 1-continued

Examples of the meaning of the grouping

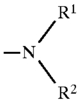

| 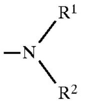 | 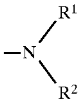 |
|---|---|
| 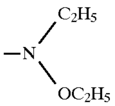 | 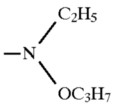 |
| 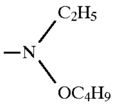 | 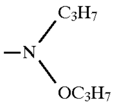 |
| 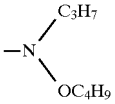 | 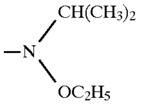 |
| 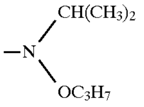 | 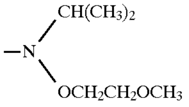 |
| 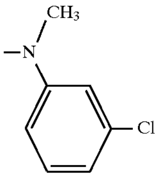 | 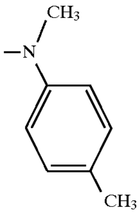 |
| 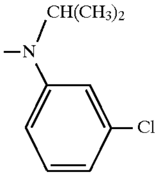 | 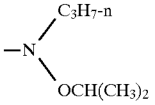 |
| 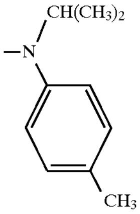 | |

The above-listed general radical definitions, or those given in preference ranges, apply both to the end products of the formula (I) and, correspondingly, to the starting compounds or intermediates which are in each case required for the preparation.

These radical definitions may be arbitrarily combined among themselves, that is also between the given ranges of preferred compounds.

If, for example, 3-methylsulphinyl-5-chloro-1,2,4-thiadiazole and N-methyl-hydroxyacetanilide are used as starting compounds, the course of the reaction in the novel process (a) can then be outlined by the following formula scheme:

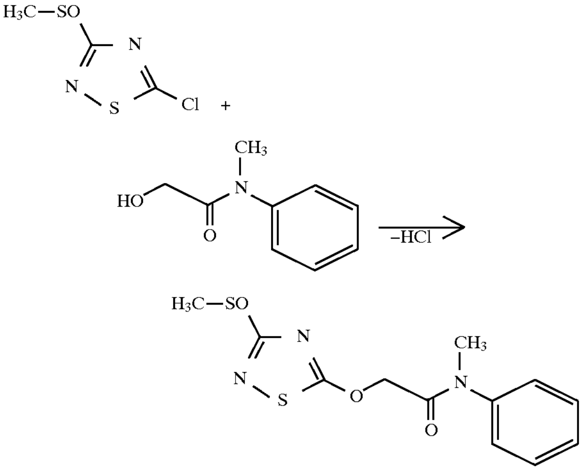

If, for example, N-cyclohexyl-N-methyl-α-(3-methylthio-1,2,4-thiadiazol-5-yl-oxy)-acetamide and hydrogen peroxide are used as starting compounds, the course of the reaction in the novel process (b) can then be outlined by the following formula scheme:

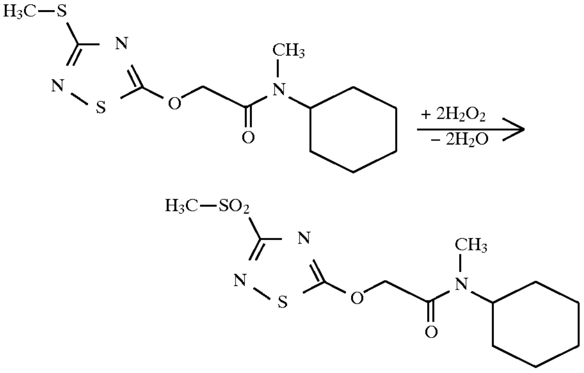

The 1,2,4-thiadiazole derivatives which are to be used as starting compounds in the novel process (a) for preparing the compounds of the general formula (I) are defined generally by the formula (II). In the formula (II), n and $R^3$ preferably or in particular have those meanings which have already been indicated above, in connection with the description of the compounds of the formula (I), as being preferred or as being particularly preferred for n and $R^3$.

With the exception of the compounds 5-chloro-3-methylsulphonyl-1,2,4-thiadiazole and 3,5-bis-methylsulphonyl-1,2,4-thiadiazole (cf. Chem. Ber. 97 (1964), 225–237; German Published Specification 1544505), the starting compounds of the formula (II) are still not disclosed in the literature and, with the exception of the abovementioned compounds, are likewise part of the subject-matter of the present application.

The 1,2,4-thiadiazole derivatives of the formula (II) are obtained if corresponding alkylthio compounds of the formula (V)

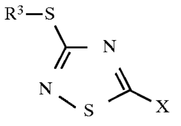

(V)

in which $R^3$ and X have the abovementioned meaning, are reacted with an oxidizing agent, for example hydrogen peroxide, where appropriate in the presence of a reaction auxiliary, for example sodium tungstate or sulphuric acid, and where appropriate in the presence of a diluent, for example water, methanol, formic acid and/or acetic acid, at temperatures of between 0° C. and 150° C. (cf. the preparation examples).

The precursors of the formula (V) are known and/or may be prepared by processes which are known per se (cf. Chem. Ber. 90 (1957), 892–901; loc. cit. 97 (1964), 225–237; East German Patent Specification 221060; preparation examples)

The hydroxyacetamides which are additionally to be used as starting compounds in the novel process (a) for preparing compounds of the formula (I) are defined generally by the formula (III).

In formula (III), $R^1$ and $R^2$ preferably or in particular have those meanings which have already been indicated above, in connection with the description of the novel compounds of the formula (I), as being preferably or particularly preferred for $R^1$ and $R^2$.

The hydroxyacetamides of the formula (III) are known and/or may be prepared by processes which are known per se (cf. U.S. Pat. No. 4509971 and U.S. Pat. No. 4645525; and, in addition, U.S. Pat. No. 4334073, DE-OS (German Published Specification) 3038598, DE-OS (German Published Specification) 3038636, EP-A 37526, EP-A 348737 and DE-OS (German Published Specification) 3819477.

The alkyl(aryl-, aralkyl-)thio-1,2,4-thiadiazolyloxyacetamides to be used as starting compounds in the novel process (b) for preparing the compounds of the general formula (I) are defined generally by the formula (IV). In the formula (IV), $R^1$, $R^2$ and $R^3$ preferably or in particular have those meanings which have already been indicated above, in connection with the description of the compounds of the formula (I), as being preferred or as being particularly preferred for $R^1$, $R^2$ and $R^3$.

The starting compounds of the formula (IV) are known and/or may be prepared by processes which are known per se (cf. EP-A 018497 and EP-A 029171).

The novel process (a) for preparing the novel alkylsulphinyl- and alkylsulphonyl-1,2,4-thiadiazolyloxyacetamides of the formula (I) is preferably carried out using diluents. These diluents preferably include hydrocarbons, for example toluene, xylene or cyclohexane, halogeno hydrocarbons, for example methylene chloride, ethylene chloride, chloroform or chlorobenzene, ethers, for example diethyl ether, dipropyl ether, diisopropyl ether, dibutyl ether, diisobutyl ether, glycol dimethyl ether, tetrahydrofuran and dioxane, alcohols, for example methanol, ethanol, propanol, isopropanol, butanol, isobutanol, sec-butanol or tert-butanol, ketones, for example acetone, methyl ethyl ketone, methyl isopropyl ketone and methyl isobutyl ketone, esters, for example methyl acetate and ethyl acetate, amides, for example dimethyl formamide, dimethylacetamide and N-methyl-pyrrolidone, nitrites, for example acetonitrile and propionitrile, sulphoxides, for example dimethyl sulphoxide, and also water or aqueous salt solutions.

In this context, the salts which are used are preferably chlorides or sulphates of alkali metals or alkaline earth metals, for example sodium chloride, potassium chloride or calcium chloride. Sodium chloride is particularly preferred.

The novel process (a) is advantageously carried out using acid-binding agents. Those which are preferably used are strongly basic alkali metal and alkaline earth metal compounds, for example oxides, for example sodium, potassium, magnesium and calcium oxide, hydroxides, for example sodium, potassium, magnesium and calcium hydroxide, alkoxides, for example sodium and potassium tert-butoxide, and/or carbonates, for example sodium, potassium, magnesium and calcium carbonate.

The addition of from 0.01 to 10% by weight (based on the glycolamide of the formula (III) which is employed) of a phase transfer catalyst may be found to be advantageous in some cases. Examples of such catalysts which may be mentioned are:

Tetrabutylammonium chloride, tetrabutylammonium bromide, tributyl-methylphosphonium bromide, trimethyl-$C_{13}/C_5$-alkyl-ammonium chloride, dibenzyl-dimethylammonium methylsulphate, dimethyl-$C_{12}/C_{14}$-alkyl-benzylammonium chloride, tetrabutylammonium hydroxide, 18-crown-6, triethylbenzylammonium chloride, trimethylbenzylammonium chloride and tetraethylammonium bromide.

In the novel process (a), the reaction temperatures may be varied over a relatively wide range. In general, the process is carried out at temperatures of between −50° C. and +110° C., preferably at temperatures of between −20° C. and +80° C.

In general, the novel process (a) is carried out under standard pressure; however, it can also be carried out under elevated or reduced pressure, between approximately 0.1 and 10 bar.

In general, in order to carry out the novel process (a), from 0.5 to 5 mol, preferably from 0.8 to 1.5 mol, of hydroxy-acetamide of the formula (III) are employed per mol of 1,2,4-thiadiazole derivative of the formula (II). The reaction components may be added together in any sequence. In each case, the reaction mixture is stirred until the reaction is complete, and working-up takes place in accordance with customary methods (cf. the preparation examples).

The novel process (b) for preparing the compounds of the formula (I) is carried out using an oxidizing agent. The customary chemicals which are suitable for oxidizing organic sulphides (thioethers) to corresponding sulphoxides or sulphones are suitable for use in this context. Examples of suitable oxidizing agents which may be mentioned are: hydrogen peroxide ($H_2O_2$), performic acid, peracetic acid, perpropionic acid, perbenzoic acid and 3-chloro-perbenzoic acid, and chlorine or hypochlorous acid and its alkali metal or alkaline earth metal salts.

The novel process (b) is optionally carried out in the presence of a catalyst. Salts of metals of the IVth, Vth and VIth subgroup of the periodic system of the elements are preferably used as catalysts in this context. Examples of these catalysts which may be mentioned are sodium (meta) vanadate, sodium molybdate and sodium tungstate.

The novel process (b) is preferably carried out using a diluent. The organic solvents which are customary for oxidation reactions are, together with water, suitable for use as diluents in this context. These solvents preferably include chlorinated hydrocarbons, such as methylene chloride, ethylene chloride, chloroform, tetrachloromethane, 1,1,2-trichloroethane, chlorobenzene and o-dichlorobenzene, alcohols, such as methanol, ethanol, propanol, isopropanol, butanol, isobutanol and sec-butanol, and carboxylic acids, such as formic acid, acetic acid and propionic acid.

In the novel process (b), the reaction temperatures may be varied over a relatively wide range. In general, the process is carried out at temperatures of between −20° C. and +60° C., preferably at temperatures of between 0° C. and 40° C.

In general, the novel process (b) is carried out under standard pressure. However, it is also possible to carry it out under elevated or reduced pressure—in general between 0.1 bar and 10 bar.

In general, in order to carry out the novel process (b), between 1 and 10 mol, preferably between 1 and 5 mol, of oxidizing agent and, where appropriate, between 0.001 and 0.1 mol, preferably between 0.01 and 0.05 mol, of a catalyst, are employed per 1 mol of starting compound of the formula (II).

In a preferred embodiment of the novel process (b), the starting compound of the formula (II) and, where appropriate a catalyst are initially introduced into a diluent, and the oxidizing agent is slowly metered in while stirring. The reaction mixture is stirred until the reaction is complete and is then worked up in a customary manner (cf. the preparation examples).

The novel active compounds can be used as defoliants, desiccants, haulm killers and, especially, as weedkillers. By weeds, in the broadest sense, there are to be understood all plants which grow in locations where they are undesired. Whether the novel compounds act as total or selective herbicides depends essentially on the amount used.

The novel active compounds can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the novel active compounds is in no way restricted to these genera, but also extends in the same manner to other plants.

Depending on the concentration, the compounds are suitable for total weed control, for example on industrial terrain and rail tracks and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The novel compounds of the formula (I) are suitable, in particular, for selectively controlling monocotyledenous and dicotyledonous weeds in dicotyledonous cultures, especially in the pre-emergence process.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and microencapsulations in polymeric substances.

These formulations are produced in a known manner, for example by mixing the novel active compounds with extenders, that is liquid solvents and/or solid carriers, optionally with the use of surface-active agents, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolyzates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the novel active compounds, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulphuron, bensulphuron-methyl, chlorimuron-ethyl, chlorsulphuron, cinosulphuron, metsulphuron-methyl, nicosulphuron, primisulphuron, pyrazosulphuron-ethyl, thifensulphuron-methyl, triasulphuron and tribenuron-methyl; thiocarbamates such as, for example, butylate, cycloate, diallate, EPTC, esprocarb, molinate, prosulphocarb, thiobencarb and triallate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufo-sinate, glyphosate, isoxaben, pyridate, quinchlorac, quinmerac, sulphosate and tridiphane.

A mixture with other known novel active compounds such as fungicides, insecticides, acaricides, nematicides, bird repellants, plant nutrients and soil conditioners, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The novel active compounds can be applied both before and after emergence of the plants. They can also be incorporated into the soil before sowing.

The amount of active compound used can vary within a relatively wide range. It depends essentially on the nature of the desired effect. In general, the rates of application are between 10 g and 10 kg of active compound per hectare of soil surface, preferably between 50 g and 5 kg per ha.

The preparation and use of the novel active compounds can be seen from the examples which follow.

PREPARATION EXAMPLES

Example 1

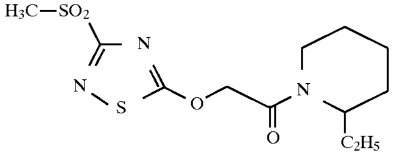

3.6 g (15 mmol) of 3,5-bis-methylsulphonyl-1,2,4-thiadiazole are dissolved, together with 2.6 g (15 mmol) of hydroxyaceto-2-ethyl-piperidide, in 40 ml of acetone. A solution of 0.6 g of sodium hydroxide in 3.3 ml of water is added dropwise to this at −20° C. The reaction mixture is stirred at −15° C. for 12 hours. It is then diluted to twice its volume with water and the whole is shaken with chloroform. The organic phase is separated off, dried with sodium sulphate and filtered. The solvent is carefully distilled off from the filtrate under a water pump vacuum.

4.8 g (77% of theory) of α-(3-methylsulphonyl-1,2,4-thiadiazol-5-yl-oxy)-aceto-2-ethyl-piperidide are obtained as an oily residue with a refracted index $N_D^{20}$=1.5329.

Example 2

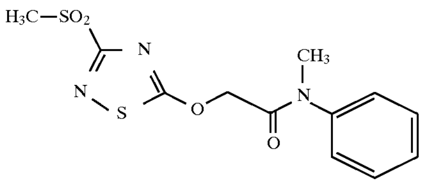

29.5 g (0.10 mol) of α-(3-methylthio-1,2,4-thiadiazol-5-yl-oxy)-aceto-N-methyl-anilide are dissolved in 50 ml of methylene chloride. After 100 ml of water has been added, 17.75 g (0.25 mol) of chlorine are passed in, while stirring, within the space of approximately 3 hours. The organic phase is then separated off, washed with water, dried with sodium sulphate and filtered. The solvent is distilled off from the filtrate under a water pump vacuum and the residue is stirred up with a little methanol; the crystalline product is isolated by filtering it off with suction.

7.0 g (21% of theory) of α-(3-methylsulphonyl-1,2,4-thiadiazol-5-yl-oxy)-aceto-N-methyl-anilide are obtained with a melting point of 82° C.

The compound of the formula (I) which are listed in the following Table 2 may also, for example, be prepared in analogy with Preparation Examples 1 and 2 and in accordance with the general description of the novel preparation processes.

TABLE 2

Examples of the compounds of the formula (I)

| Ex. No. | n | $R^1$ | $R^2$ 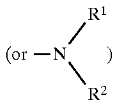 | $R^3$ | Physical data |
|---|---|---|---|---|---|
| 3 | 2 | $CH_3$ | 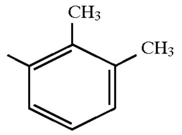 | $CH_3$ | $n_D^{20}$ = 1.5455 |
| 4 | 2 | | 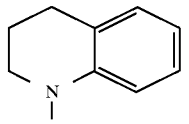 | $CH_3$ | $n_D^{20}$ = 1.5738 |
| 5 | 2 | $-CH(CH_3)_2$ | $-OCH_2CH_2OC_2H_5$ | $CH_3$ | $n_D^{20}$ = 1.5001 |
| 6 | 2 | $CH_3$ | 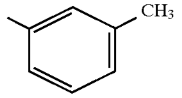 | $CH_3$ | $n_D^{20}$ = 1.5556 |
| 7 | 2 | $CH_3$ | n-$C_4H_9$ | $CH_3$ | $n_D^{20}$ = 1.5142 |
| 8 | 2 | | 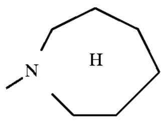 | $CH_3$ | $n_D^{20}$ = 1.5359 |
| 9 | 2 | $-CH_2-CH=CH_2$ | $-CH_2-CH=CH_2$ | $CH_3$ | $n_D^{20}$ = 1.5370 |
| 10 | 2 | $-CH(CH_3)_2$ | 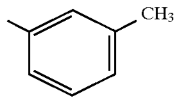 | $CH_3$ | $n_D^{20}$ = 1.5370 |
| 11 | 2 | $-CH(CH_3)_2$ | $-O-CH(CH_3)_2$ | $CH_3$ | $n_D^{20}$ = 1.5038 |
| 12 | 2 | $-CH(CH_3)_2$ | 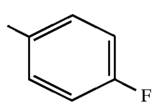 | $CH_3$ | m.p.: 70° C. |

TABLE 2-continued
Examples of the compounds of the formula (I)
| Ex. No. | n | $R^1$ | $R^2$ (or 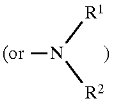 ) | $R^3$ | Physical data |
|---|---|---|---|---|---|
| 13 | 2 | $-CH(CH_3)_2$ | 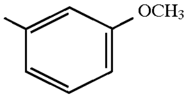 | $CH_3$ | $n_D^{20}$ = 1.5470 |
| 14 | 2 | $CH_3$ | 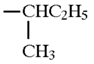 | $CH_3$ | $n_D^{20}$ = 1.5090 |
| 15 | 2 | $CH_3$ | $-CH_2OCH_3$ | $CH_3$ | $n_D^{20}$ = 1.5270 |
| 16 | 2 | | 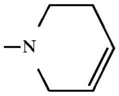 | $CH_3$ | $n_D^{20}$ = 1.5445 |
| 17 | 2 | $CH_3$ | 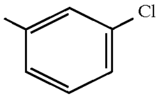 | $CH_3$ | $n_D^{20}$ = 1.5648 |
| 18 | 2 | | 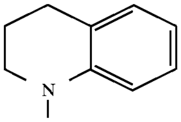 | $CH_3$ | |
| 19 | 2 | $CH_3$ | 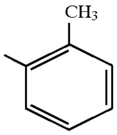 | $CH_3$ | |
| 20 | 2 | | 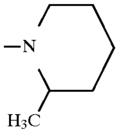 | $CH_3$ | $n_D^{20}$ = 1.5260 |
| 21 | 2 | $CH_3$ | 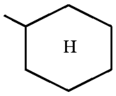 | $CH_3$ | $n_D^{20}$ = 1.5305 |
| 22 | 2 | $CH_3$ | 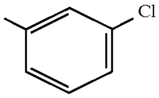 | $C_2H_5$ | $n_D^{20}$ = 1.5732 |
| 23 | 2 | $CH_3$ | 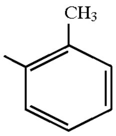 | $C_2H_5$ | $n_D^{20}$ = 1.5520 |
| 24 | 2 | $CH_3$ | 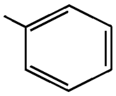 | $C_2H_5$ | $n_D^{20}$ = 1.5563 |

TABLE 2-continued

Examples of the compounds of the formula (I)

| Ex. No. | n | R$^1$ | R$^2$ (or 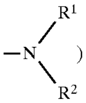 ) | R$^3$ | Physical data |
|---|---|---|---|---|---|
| 25 | 2 | $-CH(CH_3)_2$ | 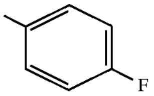 | $C_2H_5$ | $n_D^{20}$ = 1.5312 |
| 26 | 2 | $-CH(CH_3)_2$ | 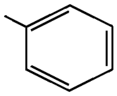 | $C_2H_5$ | $n_D^{20}$ = 1.5385 |
| 27 | 2 | $CH_3$ | 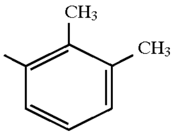 | $C_2H_5$ | $n_D^{20}$ = 1.5519 |
| 28 | 2 | 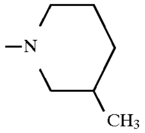 | | $C_2H_5$ | $n_D^{20}$ = 1.5269 |
| 29 | 2 | 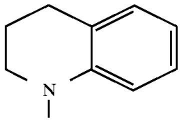 | | $C_2H_5$ | m.p.: 84° C. |
| 30 | 2 | 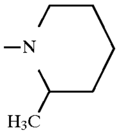 | | $C_2H_5$ | $n_D^{20}$ = 1.5058 |
| 31 | 2 | $C_2H_5$ | $C_2H_5$ | $C_2H_5$ | $n_D^{20}$ = 1.5208 |
| 32 | 2 | 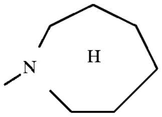 | | $C_2H_5$ | $n_D^{20}$ = 1.5319 |
| 33 | 2 | $-CH_2-CH=CH_2$ | $-CH_2-CH=CH_2$ | $C_2H_5$ | m.p.: 73° C. |
| 34 | 2 | n-$C_3H_7$ | n-$C_3H_7$ | $C_2H_5$ | $n_D^{20}$ = 1.5070 |
| 35 | 2 | 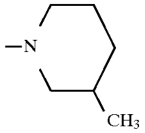 | | $C_2H_5$ | $n_D^{20}$ = 1.5311 |
| 36 | 2 | $CH_3$ | 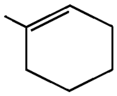 | $C_2H_5$ | $n_D^{20}$ = 1.5359 |
| 37 | 2 | $CH_3$ | 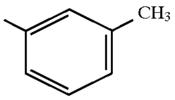 | $C_2H_5$ | $n_D^{20}$ = 1.5490 |
| 38 | 2 | $CH_3$ | n-$C_4H_9$ | $C_2H_5$ | $n_D^{20}$ = 1.5130 |
| 39 | 2 | $-CH(CH_3)_2$ | $-OCH_2CH_2OC_2H_5$ | $C_2H_5$ | $n_D^{20}$ = 1.5008 |

TABLE 2-continued
Examples of the compounds of the formula (I)
| Ex. No. | n | $R^1$ | $R^2$ 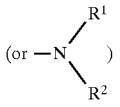 | $R^3$ | Physical data |
|---|---|---|---|---|---|
| 40 | 2 | $-CH(CH_3)_2$ | 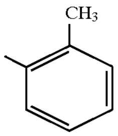 | $C_2H_5$ | $n_D^{20}$ = 1.5249 |
| 41 | 2 | $-CH(CH_3)_2$ | 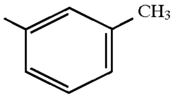 | $C_2H_5$ | $n_D^{20}$ = 1.5441 |
| 42 | 2 | $-CH(CH_3)_2$ | 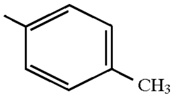 | $C_2H_5$ | m.p.: 96° C. |
| 43 | 1 | 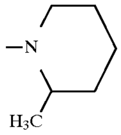 | | $CH_3$ | $n_D^{20}$ = 1.5475 |
| 44 | 1 | $-CH(CH_3)C_2H_5$ | $-OCH_3$ | $CH_3$ | $n_D^{20}$ = 1.5262 |
| 45 | 1 | $CH_3$ | 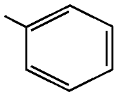 | $CH_3$ | |
| 46 | 1 | $-CH(CH_3)_2$ | 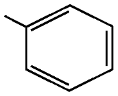 | $CH_3$ | |
| 47 | 1 | 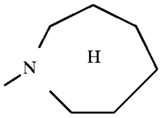 | | $CH_3$ | $n_D^{20}$ = 1.5553 |
| 48 | 1 | $-CH(CH_3)-CH(CH_3)C_2H_5$ | $-OCH_3$ | $CH_3$ | $n_D^{20}$ = 1.5104 |
| 49 | 1 | $CH_3$ | 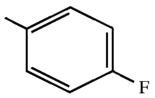 | $CH_3$ | $n_D^{20}$ = 1.5648 |
| 50 | 2 | $C_2H_5$ | $C_2H_5$ | $CH_3$ | $n_D^{20}$ = 1.5108 |
| 51 | 2 | $CH_3$ | 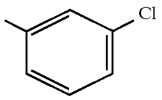 | n-$C_3H_7$ | $n_D^{20}$ = 1.5577 |

TABLE 2-continued
Examples of the compounds of the formula (I)
| Ex. No. | n | $R^1$ | $R^2$ 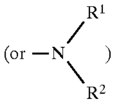 | $R^3$ | Physical data |
|---|---|---|---|---|---|
| 52 | 2 | $CH_3$ | 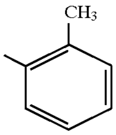 | n-$C_3H_7$ | $n_D^{20}$ = 1.5334 |
| 53 | 2 | $CH_3$ | 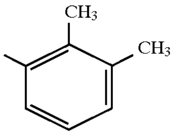 | n-$C_3H_7$ | m.p.: 79° C. |
| 54 | 2 | 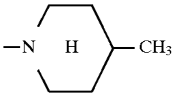 | | n-$C_3H_7$ | |
| 55 | 2 | $C_2H_5$ | $C_2H_5$ | n-$C_3H_7$ | m.p.: 73° C. |
| 56 | 2 | 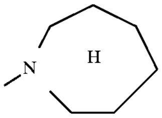 | | n-$C_3H_7$ | $n_D^{20}$ = 1.5176 |
| 57 | 2 | $-CH_2-CH=CH_2$ | $-CH_2-CH=CH_2$ | n-$C_3H_7$ | $n_D^{20}$ = 1.5129 |
| 58 | 2 | n-$C_3H_7$ | n-$C_3H_7$ | n-$C_3H_7$ | m.p.: 61° C. |
| 59 | 2 | 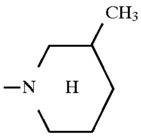 | | n-$C_3H_7$ | |
| 60 | 2 | 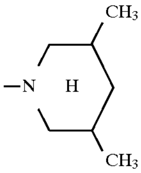 | | n-$C_3H_7$ | |
| 61 | 2 | $C_2H_5$ | 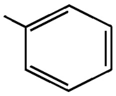 | n-$C_3H_7$ | |
| 62 | 2 | n-$C_4H_9$ | n-$C_4H_9$ | n-$C_3H_7$ | $n_D^{20}$ = 1.5043 |
| 63 | 2 | 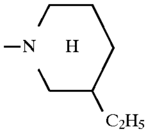 | | n-$C_3H_7$ | |
| 64 | 2 | $CH_3$ | 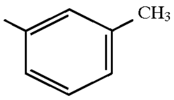 | n-$C_3H_7$ | $n_D^{20}$ = 1.5401 |
| 65 | 2 | $CH_3$ | n-$C_4H_9$ | n-$C_3H_7$ | $n_D^{20}$ = 1.5067 |

TABLE 2-continued
Examples of the compounds of the formula (I)
| Ex. No. | n | $R^1$ | $R^2$ (or 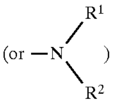 ) | $R^3$ | Physical data |
|---|---|---|---|---|---|
| 66 | 2 | $CH_3$ | 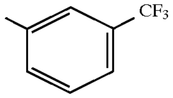 | n-$C_3H_7$ | $n_D^{20}$ = 1.5121 |
| 67 | 2 | 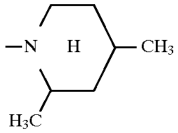 | | n-$C_3H_7$ | |
| 68 | 2 | i-$C_3H_7$ | 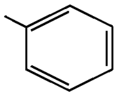 | n-$C_3H_7$ | $n_D^{20}$ = 1.5256 |
| 69 | 2 | i-$C_3H_7$ | 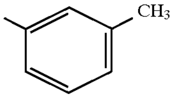 | n-$C_3H_7$ | |
| 70 | 2 | i-$C_3H_7$ | 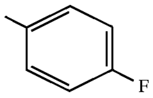 | n-$C_3H_7$ | $n_D^{20}$ = 1.5231 |
| 71 | 2 | i-$C_3H_7$ | 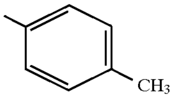 | n-$C_3H_7$ | |
| 72 | 2 | $CH_3$ | 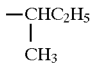 | n-$C_3H_7$ | |
| 73 | 2 | $CH_3$ | 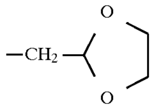 | n-$C_3H_7$ | |
| 74 | 2 | $CH_3$ | 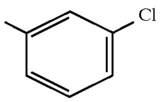 | n-$C_4H_9$ | $n_D^{20}$ = 1.5399 |
| 75 | 2 | $CH_3$ | 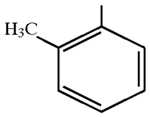 | n-$C_4H_9$ | $n_D^{20}$ = 1.5311 |
| 76 | 2 | $CH_3$ | 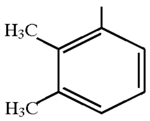 | n-$C_4H_9$ | $n_D^{20}$ = 1.5303 |
| 77 | 2 | 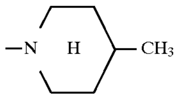 | | n-$C_4H_9$ | |
| 78 | 2 | $C_2H_5$ | $C_2H_5$ | n-$C_4H_9$ | m.p.: 84° C. |

TABLE 2-continued
Examples of the compounds of the formula (I)
| Ex. No. | n | $R^1$ | $R^2$ (or 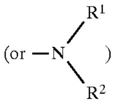) | $R^3$ | Physical data |
|---|---|---|---|---|---|
| 79 | 2 | 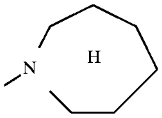 | | n-$C_4H_9$ | $n_D^{20}$ = 1.5189 |
| 80 | 2 | $-CH_2-CH=CH_2$ | $-CH_2-CH=CH_2$ | n-$C_4H_9$ | $n_D^{20}$ = 1.5262 |
| 81 | 2 | n-$C_3H_7$ | n-$C_3H_7$ | n-$C_4H_9$ | m.p.: 55° C. |
| 82 | 2 | 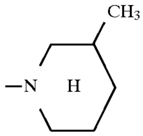 | | n-$C_4H_9$ | |
| 83 | 2 | 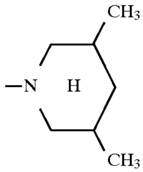 | | n-$C_4H_9$ | |
| 84 | 2 | $C_2H_5$ | 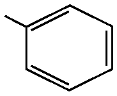 | n-$C_4H_9$ | |
| 85 | 2 | n-$C_4H_9$ | n-$C_4H_9$ | n-$C_4H_9$ | $n_D^{20}$ = 1.5021 |
| 86 | 2 | 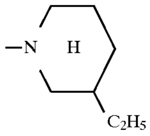 | | n-$C_4H_9$ | |
| 87 | 2 | $CH_3$ | 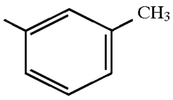 | n-$C_4H_9$ | $n_D^{20}$ = 1.5120 |
| 88 | 2 | $CH_3$ | n-$C_4H_9$ | n-$C_4H_9$ | $n_D^{20}$ = 1.4824 |
| 89 | 2 | $CH_3$ | 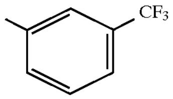 | n-$C_4H_9$ | |
| 90 | 2 | 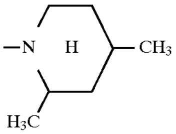 | | n-$C_4H_9$ | |
| 91 | 2 | i-$C_3H_7$ | 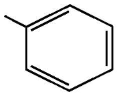 | n-$C_4H_9$ | $n_D^{20}$ = 1.5062 |
| 92 | 2 | i-$C_3H_7$ | 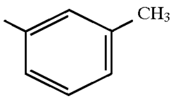 | n-$C_4H_9$ | |

TABLE 2-continued
Examples of the compounds of the formula (I)
| Ex. No. | n | $R^1$ | $R^2$ (or 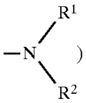 ) | $R^3$ | Physical data |
|---|---|---|---|---|---|
| 93 | 2 | i-$C_3H_7$ | 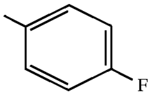 | n-$C_4H_9$ | $n_D^{20}$ = 1.5128 |
| 94 | 2 | i-$C_3H_7$ | 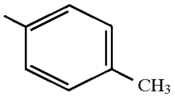 | n-$C_4H_9$ | |
| 95 | 2 | $CH_3$ | 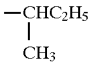 | n-$C_4H_9$ | |
| 96 | 2 | $CH_3$ | 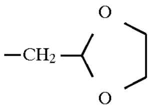 | n-$C_4H_9$ | |
| 97 | 2 | $CH_3$ | 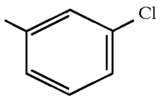 | i-$C_3H_7$ | |
| 98 | 2 | $CH_3$ | 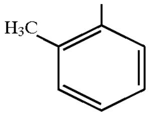 | i-$C_3H_7$ | $n_D^{20}$ = 1.5435 |
| 99 | 2 | $CH_3$ | 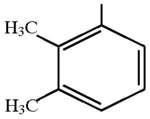 | i-$C_3H_7$ | $n_D^{20}$ = 1.5447 |
| 100 | 2 | 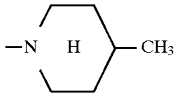 | | i-$C_3H_7$ | |
| 101 | 2 | $C_2H_5$ | $C_2H_5$ | i-$C_3H_7$ | |
| 102 | 2 | 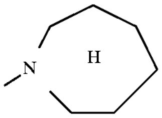 | | i-$C_3H_7$ | $n_D^{20}$ = 1.5185 |
| 103 | 2 | $-CH_2-CH=CH_2$ | $CH_2-CH=CH_2$ | i-$C_3H_7$ | $n_D^{20}$ = 1.5252 |
| 104 | 2 | n-$C_3H_7$ | n-$C_3H_7$ | i-$C_3H_7$ | |
| 105 | 2 | 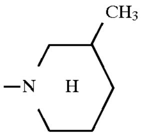 | | i-$C_3H_7$ | |
| 106 | 2 | 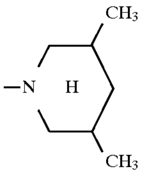 | | i-$C_3H_7$ | |

TABLE 2-continued
Examples of the compounds of the formula (I)
| Ex. No. | n | $R^1$ | $R^2$ 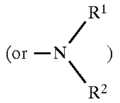 | $R^3$ | Physical data |
|---|---|---|---|---|---|
| 107 | 2 | $C_2H_5$ | 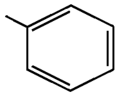 | i-$C_3H_7$ | |
| 108 | 2 | n-$C_4H_9$ | n-$C_4H_9$ | i-$C_3H_7$ | |
| 109 | 2 | 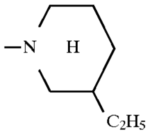 | | i-$C_3H_7$ | |
| 110 | 2 | $CH_3$ | 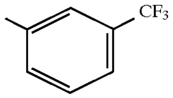 | i-$C_3H_7$ | |
| 111 | 2 | $CH_3$ | n-$C_4H_9$ | i-$C_3H_7$ | |
| 112 | 2 | $CH_3$ | 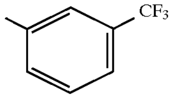 | i-$C_3H_7$ | |
| 113 | 2 | 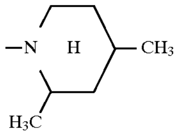 | | i-$C_3H_7$ | |
| 114 | 2 | i-$C_3H_7$ | 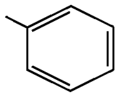 | i-$C_3H_7$ | $n_D^{20}$ = 1.5374 |
| 115 | 2 | i-$C_3H_7$ | 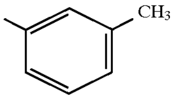 | i-$C_3H_7$ | |
| 116 | 2 | i-$C_3H_7$ | 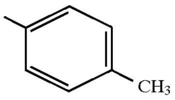 | i-$C_3H_7$ | m.p: 89° C. |
| 117 | 2 | i-$C_3H_7$ | 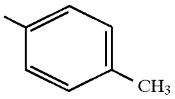 | i-$C_3H_7$ | |
| 118 | 2 | $CH_3$ | 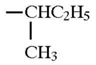 | i-$C_3H_7$ | |
| 119 | 2 | $CH_3$ | 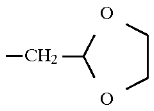 | i-$C_3H_7$ | |
| 120 | 2 | $CH_3$ | 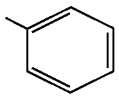 | i-$C_3H_7$ | |

TABLE 2-continued

Examples of the compounds of the formula (I)

| Ex. No. | n | $R^1$ | $R^2$ (or 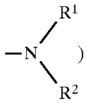 ) | $R^3$ | Physical data |
|---|---|---|---|---|---|
| 121 | 2 | $CH_3$ | 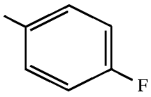 | i-$C_3H_7$ | $n_D^{20}$ = 1.5341 |
| 122 | 2 | $CH_3$ | 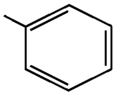 | n-$C_3H_7$ | |
| 123 | 2 | $CH_3$ | 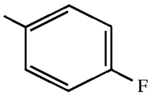 | n-$C_3H_7$ | |
| 124 | 2 | $CH_3$ | 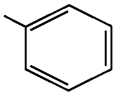 | n-$C_4H_9$ | |
| 125 | 2 | $CH_3$ | 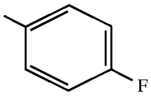 | n-$C_4H_9$ | |
| 126 | 2 | $CH_3$ | 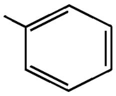 | $-CH_2CH_2-O-C_2H_5$ | |
| 127 | 2 | $CH_3$ | 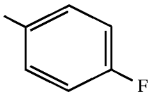 | $-CH_2CH_2-O-C_2H_5$ | |
| 128 | 2 | $C_2H_5$ | 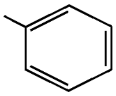 | $-CH_2CH_2-O-C_2H_5$ | |
| 129 | 2 | $CH_3$ | 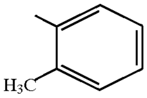 | $-CH_2CH_2-O-C_2H_5$ | $n_D^{20}$ = 1.5400 |
| 130 | 2 | i-$C_3H_7$ | 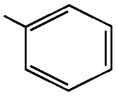 | $-CH_2CH_2-O-C_2H_5$ | |
| 131 | 2 | i-$C_3H_7$ | 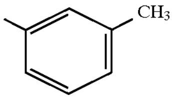 | $-CH_2CH_2-O-C_2H_5$ | |
| 132 | 2 | i-$C_3H_7$ | 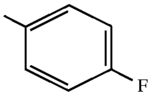 | $-CH_2CH_2-O-C_2H_5$ | |
| 133 | 2 | $C_2H_5$ | $C_2H_5$ | $-CH_2CH_2-O-C_2H_5$ | |
| 134 | 2 | n-$C_3H_7$ | n-$C_3H_7$ | $-CH_2CH_2-O-C_2H_5$ | |
| 135 | 2 | $-CH_2-CH=CH_2$ | $-CH_2-CH=CH_2$ | $-CH_2CH_2-O-C_2H_5$ | |
| 136 | 2 | n-$C_4H_9$ | n-$C_4H_9$ | $-CH_2CH_2-O-C_2H_5$ | |

TABLE 2-continued
Examples of the compounds of the formula (I)
| Ex. No. | n | $R^1$ | $R^2$ (or 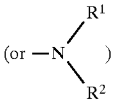) | $R^3$ | Physical data |
|---|---|---|---|---|---|
| 137 | 2 | 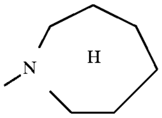 | | $-CH_2CH_2-O-C_2H_5$ | |
| 138 | 2 | 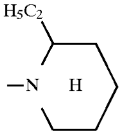 | | $-CH_2CH_2-O-C_2H_5$ | |
| 139 | 2 | 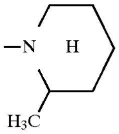 | | $-CH_2CH_2-O-C_2H_5$ | |
| 140 | 2 | $CH_3$ | n-$C_4H_9$ | $-CH_2CH_2-O-C_2H_5$ | |
| 141 | 2 | $CH_3$ | 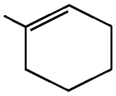 | $-CH_2CH_2-O-C_2H_5$ | |
| 142 | 2 | $CH_3$ | 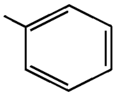 | 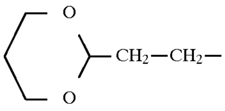 | |
| 143 | 2 | $CH_3$ | 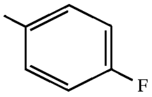 | 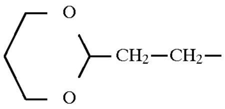 | |
| 144 | 2 | $C_2H_5$ | 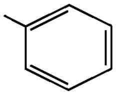 | 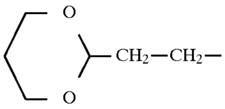 | |
| 145 | 2 | $CH_3$ | 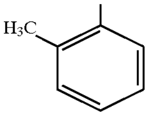 | 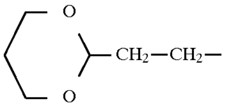 | |
| 146 | 2 | i-$C_3H_7$ | 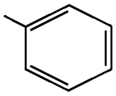 | 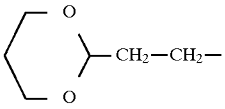 | |
| 147 | 2 | i-$C_3H_7$ | 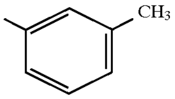 | 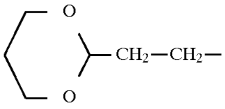 | |
| 148 | 2 | i-$C_3H_7$ | 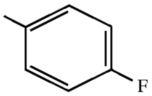 | 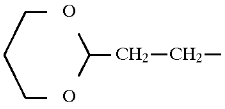 | |

TABLE 2-continued
Examples of the compounds of the formula (I)
| Ex. No. | n | $R^1$ | $R^2$ (or 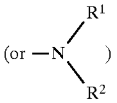) | $R^3$ | Physical data |
|---|---|---|---|---|---|
| 149 | 2 | $C_2H_5$ | $C_2H_5$ | 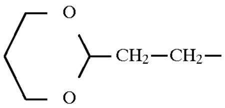 | |
| 150 | 2 | n-$C_3H_7$ | n-$C_3H_7$ | 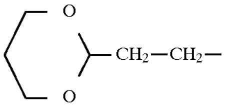 | |
| 151 | 2 | $-CH_2-CH=CH_2$ | $-CH_2-CH=CH_2$ | 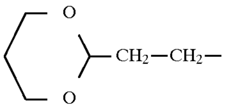 | |
| 152 | 2 | n-$C_4H_9$ | n-$C_4H_9$ | 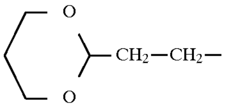 | |
| 153 | 2 | 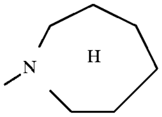 | | 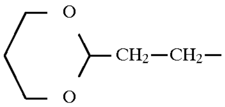 | |
| 154 | 2 | 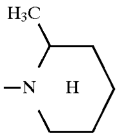 | | 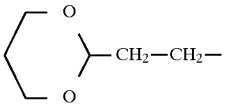 | |
| 155 | 2 | 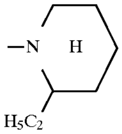 | | 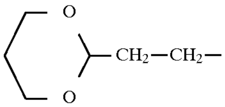 | |
| 156 | 2 | $CH_3$ | n-$C_4H_9$ | 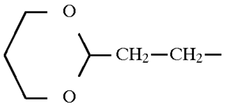 | |
| 157 | 2 | $CH_3$ | 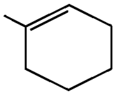 | 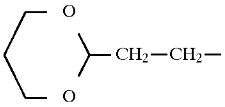 | |
| 158 | 2 | $CH_3$ | 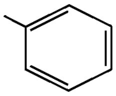 | 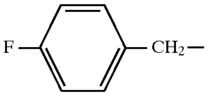 | |
| 159 | 2 | $CH_3$ | 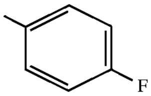 | 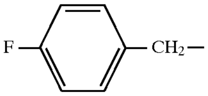 | |
| 160 | 2 | $C_2H_5$ | 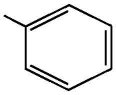 | 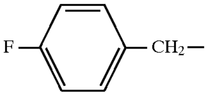 | |

TABLE 2-continued
Examples of the compounds of the formula (I)
| Ex. No. | n | $R^1$ | $R^2$ (or 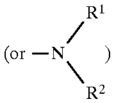) | $R^3$ | Physical data |
|---|---|---|---|---|---|
| 161 | 2 | $CH_3$ | 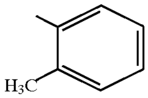 | 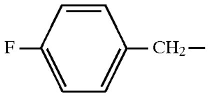 | m.p.: 127° C. |
| 162 | 2 | i-$C_3H_7$ | 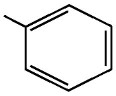 | 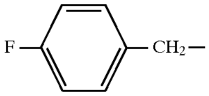 | |
| 163 | 2 | i-$C_3H_7$ | 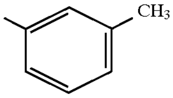 | 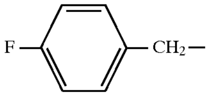 | |
| 164 | 2 | i-$C_3H_7$ | 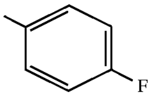 | 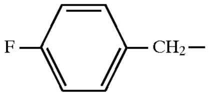 | |
| 165 | 2 | $C_2H_5$ | $C_2H_5$ | 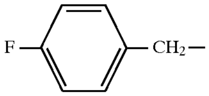 | |
| 166 | 2 | n-$C_3H_7$ | n-$C_3H_7$ | 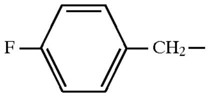 | |
| 167 | 2 | $-CH_2-CH=CH_2$ | $-CH_2-CH=CH_2$ | 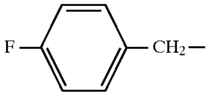 | |
| 168 | 2 | n-$C_4H_9$ | n-$C_4H_9$ | 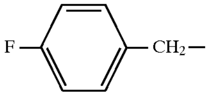 | |
| 169 | 2 | 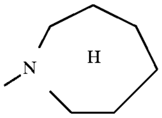 | | 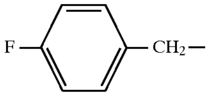 | |
| 170 | 2 | 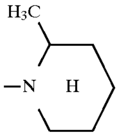 | | 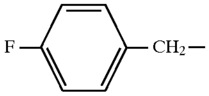 | |
| 171 | 2 | 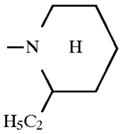 | | 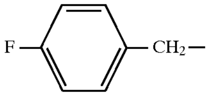 | |
| 172 | 2 | $CH_3$ | n-$C_4H_9$ | 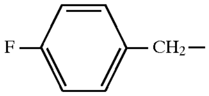 | |

TABLE 2-continued
Examples of the compounds of the formula (I)
| Ex. No. | n | $R^1$ | $R^2$ (or 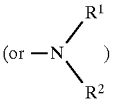) | $R^3$ | Physical data |
|---|---|---|---|---|---|
| 173 | 2 | $CH_3$ | 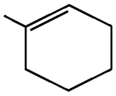 | 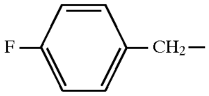 | |
| 174 | 2 | $CH_3$ | 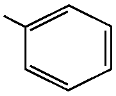 | 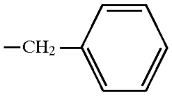 | |
| 175 | 2 | $CH_3$ | 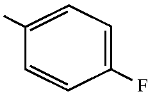 | 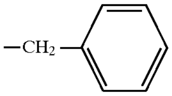 | |
| 176 | 2 | $C_2H_5$ | 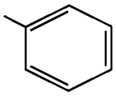 | 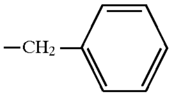 | |
| 177 | 2 | $CH_3$ | 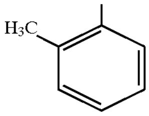 | 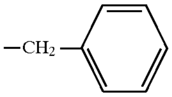 | |
| 178 | 2 | $i-C_3H_7$ | 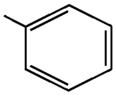 | 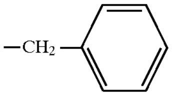 | |
| 179 | 2 | $i-C_3H_7$ | 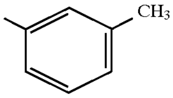 | 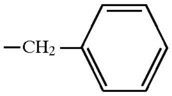 | |
| 180 | 2 | $i-C_3H_7$ | 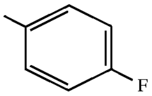 | 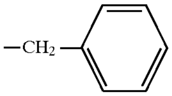 | |
| 181 | 2 | $C_2H_5$ | $C_2H_5$ | 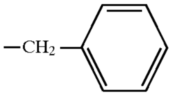 | |
| 182 | 2 | $n-C_3H_7$ | $n-C_3H_7$ | 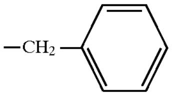 | |
| 183 | 2 | $-CH_2-CH=CH_2$ | $-CH_2-CH=CH_2$ | 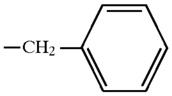 | |
| 184 | 2 | $n-C_4H_9$ | $n-C_4H_9$ | 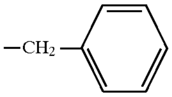 | |
| 185 | 2 | 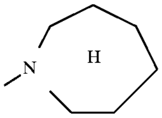 | | 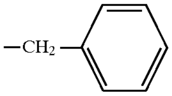 | |

TABLE 2-continued
Examples of the compounds of the formula (I)
| Ex. No. | n | $R^1$ | $R^2$ (or 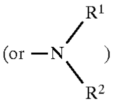) | $R^3$ | Physical data |
|---|---|---|---|---|---|
| 186 | 2 | 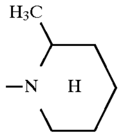 | | 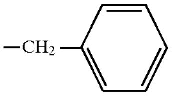 | |
| 187 | 2 | 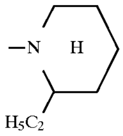 | | 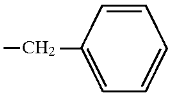 | |
| 188 | 2 | $CH_3$ | n-$C_4H_9$ | 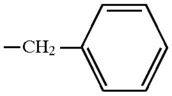 | |
| 189 | 2 | $CH_3$ | 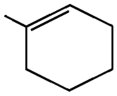 | 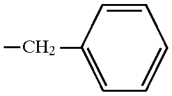 | |
| 190 | 2 | $CH_3$ | $CH(CH_3)_2$ | $C_2H_5$ | $n_D^{20}$ = 1.5192 |
| 191 | 2 | $CH_3$ | $CH(CH_3)_2$ | $CH_3$ | $n_D^{20}$ = 1.5075 |
| 192 | 2 | $CH(CH_3)_2$ | 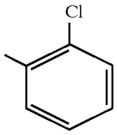 | $CH_3$ | $n_D^{20}$ = 1.5603 |
| 193 | 2 | $CH_3$ | 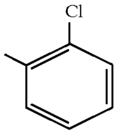 | $CH_3$ | $n_D^{20}$ = 1.5440 |
| 194 | 2 | $CH(CH_3)_2$ | 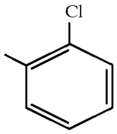 | $C_2H_5$ | $n_D^{20}$ = 1.5362 |
| 195 | 2 | $CH_3$ | 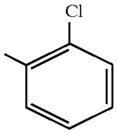 | $C_2H_5$ | $n_D^{20}$ = 1.5230 |
| 196 | 2 | $CH_3$ | 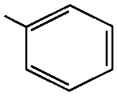 | n-$C_3H_7$ | $n_D^{20}$ = 1.5402 |
| 197 | 2 | 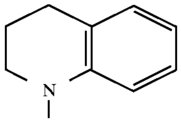 | | n-$C_3H_7$ | m.p.: 112° C. |

TABLE 2-continued
Examples of the compounds of the formula (I)
| Ex. No. | n | $R^1$ | $R^2$ 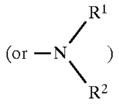 | $R^3$ | Physical data |
|---|---|---|---|---|---|
| 198 | 2 | | 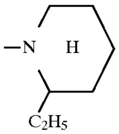 | n-$C_3H_7$ | $n_D^{20}$ = 1.5192 |
| 199 | 2 | | 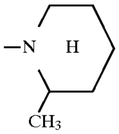 | n-$C_3H_7$ | $n_D^{20}$ = 1.5122 |
| 200 | 2 | $CH_3$ | 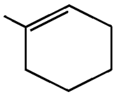 | n-$C_3H_7$ | $n_D^{20}$ = 1.5306 |
| 201 | 2 | $CH(CH_3)_2$ | $-OC_2H_4OC_2H_5$ | n-$C_3H_7$ | $n_D^{20}$ = 1.4853 |
| 202 | 2 | $CH(CH_3)_2$ | 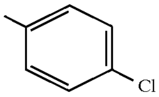 | n-$C_3H_7$ | $n_D^{20}$ = 1.5299 |
| 203 | 2 | $CH_3$ | 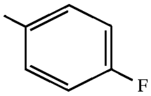 | n-$C_3H_7$ | $n_D^{20}$ = 1.5351 |
| 204 | 2 | $C_2H_5$ | 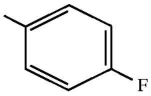 | n-$C_3H_7$ | $n_D^{20}$ = 1.5084 |
| 205 | 2 | | 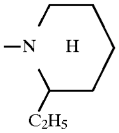 | n-$C_4H_9$ | $n_D^{20}$ = 1.5148 |
| 206 | 2 | | 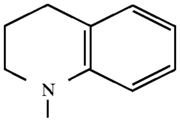 | n-$C_4H_9$ | m.p.: 121° C. |
| 207 | 2 | $CH_3$ | 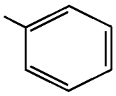 | n-$C_4H_9$ | $n_D^{20}$ = 1.5245 |
| 208 | 2 | | 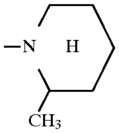 | n-$C_4H_9$ | m.p.: 85° C. |
| 209 | 2 | $CH_3$ | 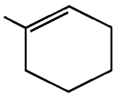 | n-$C_4H_9$ | $n_D^{20}$ = 1.5148 |

TABLE 2-continued
Examples of the compounds of the formula (I)
| Ex. No. | n | $R^1$ | $R^2$ (or 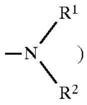 ) | $R^3$ | Physical data |
|---|---|---|---|---|---|
| 210 | 2 | $CH(CH_3)_2$ | $-OC_2H_4OC_2H_5$ | $n-C_4H_9$ | $n_D^{20}$ = 1.4908 |
| 211 | 2 | $CH(CH_3)_2$ | 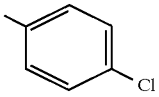 | $n-C_4H_9$ | $n_D^{20}$ = 1.5251 |
| 212 | 2 | $CH_3$ | 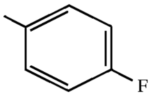 | $n-C_4H_9$ | $n_D^{20}$ = 1.5309 |
| 213 | 2 | $C_2H_5$ | 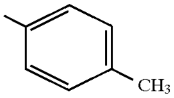 | $n-C_4H_9$ | $n_D^{20}$ = 1.5287 |
| 214 | 2 | $C_2H_5$ | 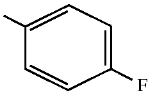 | $n-C_4H_9$ | $n_D^{20}$ = 1.5287 |
| 215 | 2 | $C_2H_5$ | $n-C_4H_9$ | $CH_3$ | m.p.: 56° C. |
| 216 | 2 | $C_2H_5$ | $n-C_4H_9$ | $C_2H_5$ | m.p.: 68° C. |
| 217 | 2 | $n-C_3H_7$ | 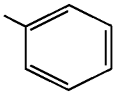 | $C_2H_5$ | $n_D^{20}$ = 1.5419 |
| 218 | 2 | $CH_3$ | 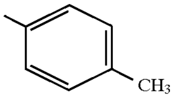 | $C_2H_5$ | $n_D^{20}$ = 1.5485 |
| 219 | 2 | | 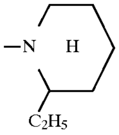 | $i-C_3H_7$ | $n_D^{20}$ = 1.5246 |
| 220 | 2 | $CH_3$ | 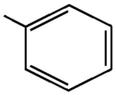 | $i-C_3H_7$ | m.p.: 120° C. |
| 221 | 2 | | 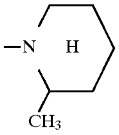 | $i-C_3H_7$ | $n_D^{20}$ = 1.5208 |
| 222 | 2 | $C_2H_5$ | 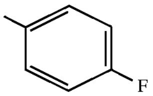 | $i-C_3H_7$ | $n_D^{20}$ = 1.5328 |
| 223 | 2 | $CH_3$ | 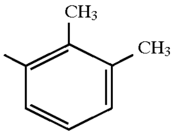 | $i-C_4H_9$ | m.p.: 70° C. |

TABLE 2-continued

Examples of the compounds of the formula (I)

| Ex. No. | n | $R^1$ | $R^2$ (or 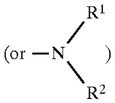) | $R^3$ | Physical data |
|---|---|---|---|---|---|
| 224 | 2 | | 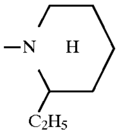 | i-$C_4H_9$ | $n_D^{20}$ = 1.4965 |
| 225 | 2 | $CH_3$ | 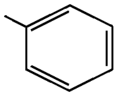 | i-$C_4H_9$ | m.p.: 68° C. |
| 226 | 2 | | 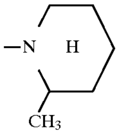 | i-$C_4H_9$ | $n_D^{20}$ = 1.4963 |
| 227 | 2 | | 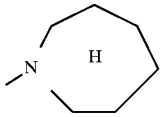 | i-$C_4H_9$ | $n_D^{20}$ = 1.4992 |
| 228 | 2 | $-CH_2-CH=CH_2$ | $-CH_2-CH=CH_2$ | i-$C_4H_9$ | $n_D^{20}$ = 1.5136 |
| 229 | 2 | $CH(CH_3)_2$ | 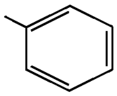 | i-$C_4H_9$ | $n_D^{20}$ = 1.5248 |
| 230 | 2 | $CH(CH_3)_2$ | 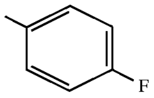 | i-$C_4H_9$ | $n_D^{20}$ = 1.5212 |
| 231 | 2 | $CH_3$ | 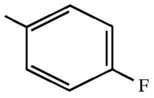 | i-$C_4H_9$ | $n_D^{20}$ = 1.5243 |
| 232 | 2 | $C_2H_5$ | 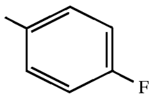 | i-$C_4H_9$ | $n_D^{20}$ = 1.5243 |
| 233 | 2 | $CH_3$ | 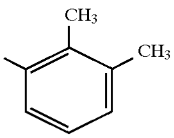 | 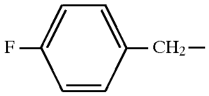 | m.p.: 117° C. |
| 234 | 2 | $CH_3$ | 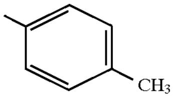 | n-$C_3H_7$ | $n_D^{20}$ = 1.5561 |
| 235 | 2 | $C_2H_5$ | n-$C_4H_9$ | n-$C_3H_7$ | $n_D^{20}$ = 1.5089 |
| 236 | 2 | n-$C_3H_7$ | 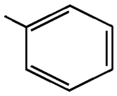 | n-$C_4H_9$ | $n_D^{20}$ = 1.5416 |
| 237 | 2 | $C_2H_5$ | n-$C_4H_9$ | $-C_2H_4OC_2H_5$ | $n_D^{20}$ = 1.5033 |

TABLE 2-continued
Examples of the compounds of the formula (I)
| Ex. No. | n | $R^1$ | $R^2$ (or 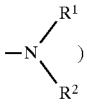 ) | $R^3$ | Physical data |
|---|---|---|---|---|---|
| 238 | 2 | | 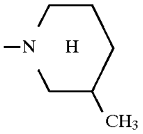 | $-C_2H_4OC_2H_5$ | $n_D^{20}$ = 1.5072 |
| 239 | 2 | $CH_3$ | 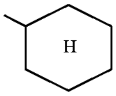 | $-C_2H_4OC_2H_5$ | $n_D^{20}$ = 1.5154 |
| 240 | 2 | $CH_3$ | 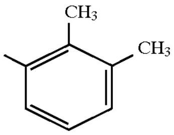 | $-C_2H_4OC_2H_5$ | m.p.: 68° C. |
| 241 | 2 | n-$C_3H_7$ | 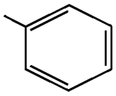 | $-C_2H_4OC_2H_5$ | $n_D^{20}$ = 1.5306 |
| 242 | 2 | | 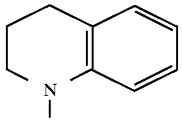 | $-C_2H_4OC_2H_5$ | $n_D^{20}$ = 1.5579 |
| 243 | 2 | $CH_3$ | 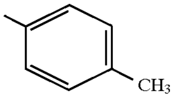 | $-C_2H_4OC_2H_5$ | m.p.: 54° C. |
| 244 | 2 | $CH_3$ | 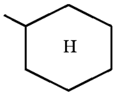 | n-$C_3H_7$ | $n_D^{20}$ = 1.5289 |
| 245 | 2 | i-$C_4H_9$ | 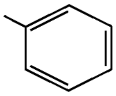 | $CH_3$ | $n_D^{20}$ = 1.5387 |
| 246 | 2 | i-$C_4H_9$ | 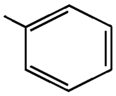 | $CH_3$ | $n_D^{20}$ = 1.5465 |
| 247 | 2 | | 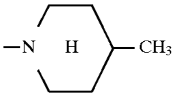 | $CH_3$ | $n_D^{20}$ = 1.5272 |
| 248 | 2 | | 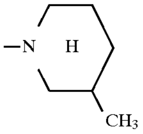 | $CH_3$ | $n_D^{20}$ = 1.5331 |

TABLE 2-continued
Examples of the compounds of the formula (I)
| Ex. No. | n | $R^1$ | $R^2$ 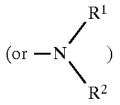 | $R^3$ | Physical data |
|---|---|---|---|---|---|
| 249 | 2 | $CH_3$ | 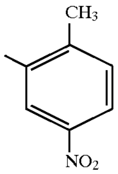 | $CH_3$ | m.p.: 223° C. |
| 250 | 2 | $CH_3$ | $-CH_2C_6H_5$ | $CH_3$ | $n_D^{20}$ = 1.5425 |
| 251 | 2 | n-$C_3H_7$ | n-$C_3H_7$ | $CH_3$ | m.p.: 56° C. |
| 252 | 2 | $CH(CH_3)_2$ | 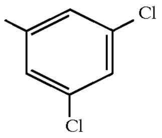 | $CH_3$ | $n_D^{20}$ = 1.5436 |
| 253 | 2 | $CH(CH_3)_2$ | 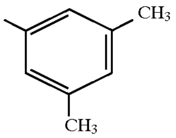 | $CH_3$ | Fp.: 72° C. |
| 254 | 2 | $CH(CH_3)_2$ | 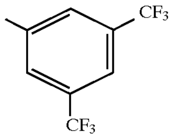 | $CH_3$ | m.p.: 91° C. |
| 255 | 2 | $CH(CH_3)_2$ | 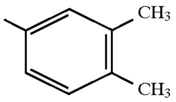 | $CH_3$ | m.p.: 87° C. |
| 256 | 2 | $CH(CH_3)_2$ | 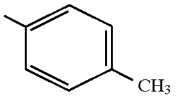 | $CH_3$ | m.p.: 115° C. |
| 257 | 2 | $CH(CH_3)_2$ | 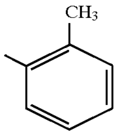 | $CH_3$ | m.p.: 98° C. |
| 258 | 2 | $CH(CH_3)_2$ | 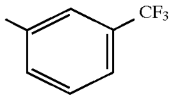 | $CH_3$ | m.p.: 86° C. |
| 259 | 2 | $-C_2H_4OCH_3$ | $-C_2H_4OCH_3$ | $CH_3$ | $n_D^{20}$ = 1.5133 |
| 260 | 2 | 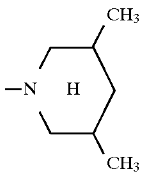 | | $CH_3$ | $n_D^{20}$ = 1.5175 |

TABLE 2-continued
Examples of the compounds of the formula (I)
| Ex. No. | n | $R^1$ | $R^2$ (or 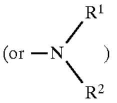) | $R^3$ | Physical data |
|---|---|---|---|---|---|
| 261 | 2 | $C_2H_5$ | 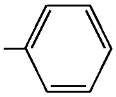 | $CH_3$ | m.p: 73° C. |
| 262 | 2 | 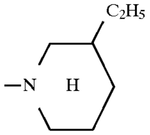 | | $CH_3$ | $n_D^{20}$ = 1.5338 |
| 263 | 2 | $CH_3$ | $-CH_2-CF_3$ | $CH_3$ | m.p.: 123° C. |
| 264 | 2 | $CH_3$ | 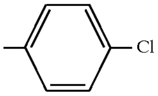 | $CH_3$ | $n_D^{20}$ = 1.5617 |
| 265 | 2 | $CH_3$ | 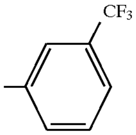 | $CH_3$ | $n_D^{20}$ = 1.5187 |
| 266 | 2 | $-OCH_3$ | 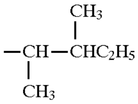 | $CH_3$ | $n_D^{20}$ = 1.5096 |
| 267 | 2 | 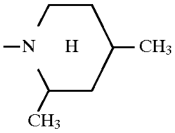 | | $CH_3$ | m.p.: 80° C. |
| 268 | 2 | i-$C_3H_7$ | 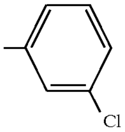 | $CH_3$ | $n_D^{20}$ = 1.5496 |
| 269 | 2 | i-$C_3H_7$ | 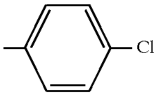 | $CH_3$ | m.p.: 74° C. |
| 270 | 2 | i-$C_3H_7$ | 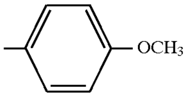 | $CH_3$ | $n_D^{20}$ = 1.5392 |
| 271 | 2 | i-$C_3H_7$ | 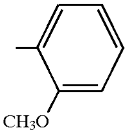 | $CH_3$ | m.p.: 105° C. |
| 272 | 2 | i-$C_3H_7$ | 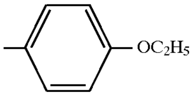 | $CH_3$ | $n_D^{20}$ = 1.5355 |

TABLE 2-continued
Examples of the compounds of the formula (I)
| Ex. No. | n | $R^1$ | $R^2$ (or 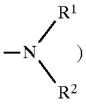) | $R^3$ | Physical data |
|---|---|---|---|---|---|
| 273 | 2 | 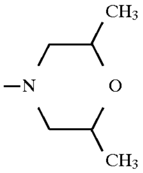 | | $CH_3$ | $n_D^{20}$ = 1.5067 |
| 274 | 2 | i-$C_3H_7$ | 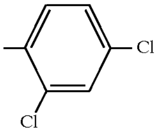 | $CH_3$ | $n_D^{20}$ = 1.5415 |
| 275 | 2 | 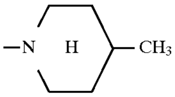 | | $C_2H_5$ | $n_D^{20}$ = 1.5308 |
| 276 | 2 | $-CH_2-CH(CH_3)_2$ | 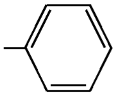 | $C_2H_5$ | $n_D^{20}$ = 1.5599 |
| 277 | 2 | $-(CH_2)_3CH_3$ | 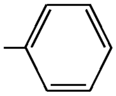 | $C_2H_5$ | $n_D^{20}$ = 1.5493 |
| 278 | 2 | $CH_3$ | 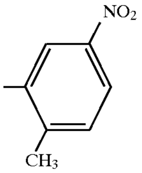 | $C_2H_5$ | m.p.: 114° C. |
| 279 | 2 | 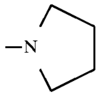 | | $C_2H_5$ | $n_D^{20}$ = 1.5366 |
| 280 | 2 | $C_2H_5$ | 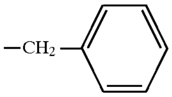 | $CH_3$ | $n_D^{20}$ = 1.5329 |
| 281 | 2 | $CH_3$ | 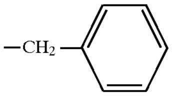 | $C_2H_5$ | $n_D^{20}$ = 1.5482 |
| 282 | 2 | $-CH_2CH_2CH_2CH_3$ | $-CH_2CH_2CH_2CH_3$ | $C_2H_5$ | $n_D^{20}$ = 1.5113 |
| 283 | 2 | $CH_3$ | i-$C_3H_7$ | n-$C_3H_7$ | $n_D^{20}$ = 1.5249 |
| 284 | 2 | $CH_3$ | 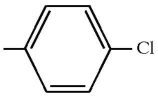 | $C_2H_5$ | $n_D^{20}$ = 1.5766 |

TABLE 2-continued
Examples of the compounds of the formula (I)
| Ex. No. | n | $R^1$ | $R^2$ (or 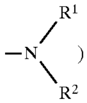 ) | $R^3$ | Physical data |
|---|---|---|---|---|---|
| 285 | 2 | $CH_3$ | 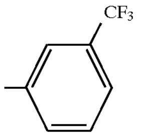 | $C_2H_5$ | $n_D^{20} = 1.5248$ |
| 286 | 2 | $-OCH_3$ | 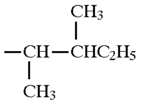 | $C_2H_5$ | $n_D^{20} = 1.5052$ |
| 287 | 2 | 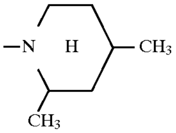 | | $C_2H_5$ | $n_D^{20} = 1.5284$ |
| 288 | 2 | $i\text{-}C_3H_7$ | 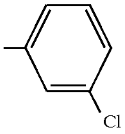 | $C_2H_5$ | $n_D^{20} = 1.5461$ |
| 289 | 2 | $i\text{-}C_3H_7$ | 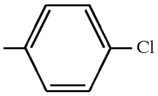 | $C_2H_5$ | $n_D^{20} = 1.5430$ |
| 290 | 2 | $i\text{-}C_3H_7$ | 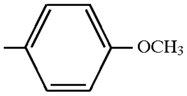 | $C_2H_5$ | $n_D^{20} = 1.5367$ |
| 291 | 2 | $i\text{-}C_3H_7$ | 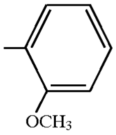 | $C_2H_5$ | $n_D^{20} = 1.5424$ |
| 292 | 2 | $i\text{-}C_3H_7$ | 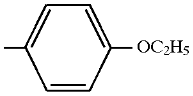 | $C_2H_5$ | $n_D^{20} = 1.5354$ |
| 293 | 2 | $i\text{-}C_3H_7$ | $-O-CH(CH_3)_2$ | $C_2H_5$ | $n_D^{20} = 1.5066$ |
| 294 | 2 | $i\text{-}C_3H_7$ | 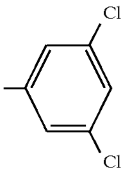 | $C_2H_5$ | $n_D^{20} = 1.5325$ |
| 295 | 2 | $i\text{-}C_3H_7$ | 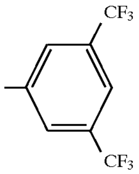 | $C_2H_5$ | $n_D^{20} = 1.4842$ |

TABLE 2-continued
Examples of the compounds of the formula (I)
| Ex. No. | n | $R^1$ | $R^2$ (or 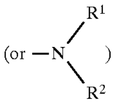) | $R^3$ | Physical data |
|---|---|---|---|---|---|
| 296 | 2 | i-$C_3H_7$ | 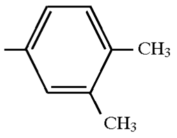 | $C_2H_5$ | $n_D^{20}$ = 1.5384 |
| 297 | 2 | i-$C_3H_7$ | 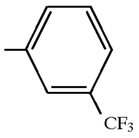 | $C_2H_5$ | $n_D^{20}$ = 1.5108 |
| 298 | 2 | $-CH_2CH_2OCH_3$ | $-CH_2CH_2OCH_3$ | $C_2H_5$ | $n_D^{20}$ = 1.5093 |
| 299 | 2 | $CH_3$ | 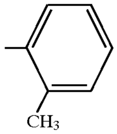 | $(CH_3)_2CHCH_2$ | m.p.: 67° C. |
| 300 | 2 | i-$C_3H_7$ | 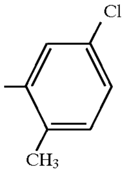 | $CH_3$ | m.p.: 78° C. |
| 301 | 2 | n-$C_4H_9$ | n-$C_4H_9$ | $CH_3$ | $n_D^{20}$ = 1.5284 |
| 302 | 2 | | 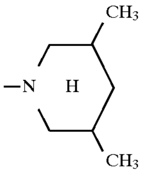 | $C_2H_5$ | $n_D^{20}$ = 1.5137 |
| 303 | 2 | $CH_3$ | i-$C_3H_7$ | i-$C_3H_7$ | $n_D^{20}$ = 1.5189 |
| 304 | 2 | $CH_3$ | i-$C_3H_7$ | 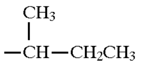 | $n_D^{20}$ = 1.5046 |
| 305 | 2 | i-$C_3H_7$ | 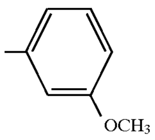 | $C_2H_5$ | $n_D^{20}$ = 1.5482 |
| 306 | 2 | i-$C_3H_7$ | 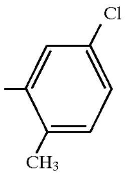 | $C_2H_5$ | $n_D^{20}$ = 1.5414 |
| 307 | 2 | $CH_3$ | 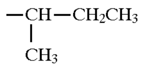 | $C_2H_5$ | $n_D^{20}$ = 1.5055 |

TABLE 2-continued
Examples of the compounds of the formula (I)
| Ex. No. | n | $R^1$ | $R^2$ (or 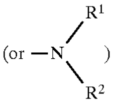) | $R^3$ | Physical data |
|---|---|---|---|---|---|
| 308 | 2 | | 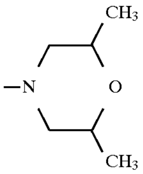 | $C_2H_5$ | $n_D^{20}$ = 1.5184 |
| 309 | 2 | n-$C_3H_7$ | 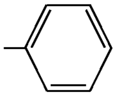 | $CH_3$ | m.p.: 73° C. |
| 310 | 2 | $CH_3$ | 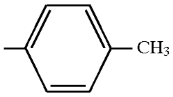 | $CH_3$ | $n_D^{20}$ = 1.5598 |
| 311 | 2 | $CH_3$ | 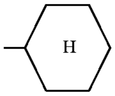 | n-$C_4H_9$ | $n_D^{20}$ = 1.5248 |
| 312 | 2 | $C_2H_5$ | n-$C_4H_9$ | n-$C_4H_9$ | $n_D^{20}$ = 1.5248 |
| 313 | 2 | $CH_3$ | 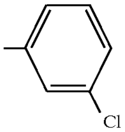 | $-C_2H_4OC_2H_5$ | m.p.: 98° C. |
| 314 | 2 | $CH_3$ | 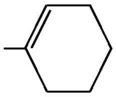 | $CH_3$ | m.p.: 87° C. |
| 315 | 2 | | 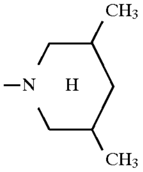 | $CH_3$ | $n_D^{20}$ = 1.5175 |
| 316 | 2 | $C_2H_5$ | 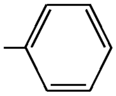 | $CH_3$ | m.p.: 73° C. |
| 317 | 2 | | 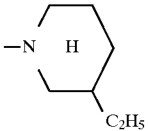 | $CH_3$ | $n_D^{20}$ = 1.5338 |
| 318 | 2 | $CH_3$ | $-CH_2-CF_3$ | $CH_3$ | m.p.: 123° C. |
| 319 | 2 | $CH_3$ | 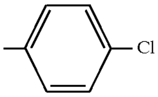 | $CH_3$ | $n_D^{20}$ = 1.5617 |

TABLE 2-continued
Examples of the compounds of the formula (I)
| Ex. No. | n | $R^1$ | $R^2$ 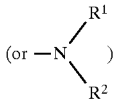 | $R^3$ | Physical data |
|---|---|---|---|---|---|
| 320 | 2 | $CH_3$ | 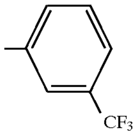 | $CH_3$ | $n_D^{20}$ = 1.5187 |
| 321 | 2 | $OCH_3$ | 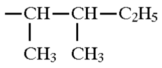 | $CH_3$ | $n_D^{20}$ = 1.5096 |
| 322 | 2 | | 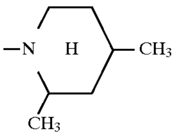 | $CH_3$ | m.p.: 80° C. |
| 323 | 2 | $CH(CH_3)_2$ | 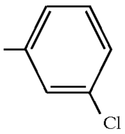 | $CH_3$ | $n_D^{20}$ = 1.5496 |
| 324 | 2 | $CH(CH_3)_2$ | 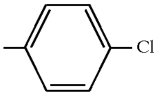 | $CH_3$ | m.p.: 74° C. |
| 325 | 2 | $CH(CH_3)_2$ | 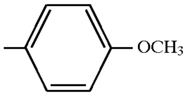 | $CH_3$ | $n_D^{20}$ = 1.5392 |
| 326 | 2 | $CH(CH_3)_2$ | 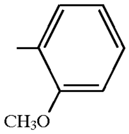 | $CH_3$ | m.p.: 105° C. |
| 327 | 2 | $CH(CH_3)_2$ | 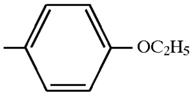 | $CH_3$ | $n_D^{20}$ = 1.5355 |
| 328 | 2 | | 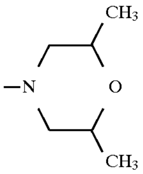 | $CH_3$ | $n_D^{20}$ = 1.5067 |
| 329 | 2 | $C_2H_5$ | 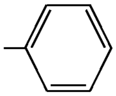 | $CH_3$ | $n_D^{20}$ = 1.5329 |
| 330 | 2 | $CH(CH_3)_2$ | 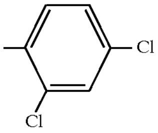 | $CH_3$ | $n_D^{20}$ = 1.5415 |

TABLE 2-continued
Examples of the compounds of the formula (I)
| Ex. No. | n | $R^1$ (or 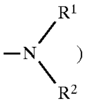 ) | $R^2$ | $R^3$ | Physical data |
|---|---|---|---|---|---|
| 331 | 2 | 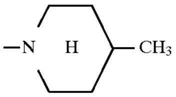 | | $C_2H_5$ | $n_D^{20}$ = 1.5308 |
| 332 | 2 | $CH_2CH(CH_3)_2$ | 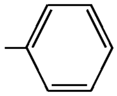 | $C_2H_5$ | $n_D^{20}$ = 1.5599 |
| 333 | 2 | n-$C_4H_9$ | 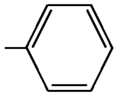 | $C_2H_5$ | $n_D^{20}$ = 1.5493 |
| 334 | 2 | $C_2H_5$ | n-$C_4H_9$ | $CHF_2$ | |
| 335 | 2 | 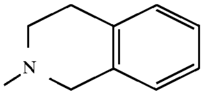 | | $CHF_2$ | |
| 336 | 2 | 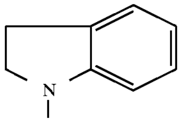 | | $CHF_2$ | |
| 337 | 2 | 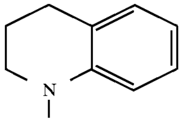 | | $CHF_2$ | |
| 338 | 2 | 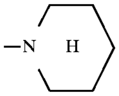 | | $CHF_2$ | |
| 339 | 2 | $CH_3$ | 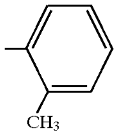 | $CHF_2$ | |
| 340 | 2 | $CH_3$ | 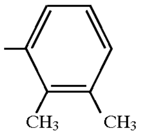 | $CHF_2$ | |
| 341 | 2 | 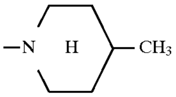 | | $CHF_2$ | |
| 342 | 2 | 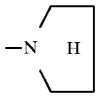 | | $CHF_2$ | |
| 343 | 2 | $C_2H_5$ | $C_2H_5$ | $CHF_2$ | |

TABLE 2-continued
Examples of the compounds of the formula (I)
| Ex. No. | n | $R^1$ | $R^2$ 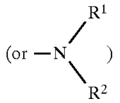 | $R^3$ | Physical data |
|---|---|---|---|---|---|
| 344 | 2 | | 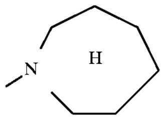 | $CHF_2$ | |
| 345 | 2 | $CH_3$ | n-$C_4H_9$ | $CHF_2$ | |
| 346 | 2 | $C_2H_5$ | 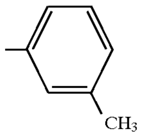 | $CHF_2$ | |
| 347 | 2 | $CH_3$ | 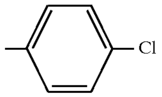 | $CHF_2$ | |
| 348 | 2 | $CH_3$ | 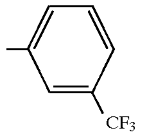 | $CHF_2$ | |
| 349 | 2 | $CH_3$ | 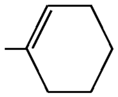 | $CHF_2$ | |
| 350 | 2 | $OCH_3$ | 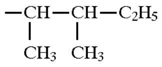 | $CHF_2$ | |
| 351 | 2 | | 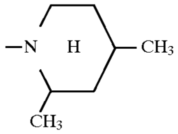 | $CHF_2$ | |
| 352 | 2 | $CH(CH_3)_2$ | 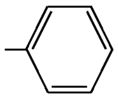 | $CHF_2$ | |
| 353 | 2 | $CH(CH_3)_2$ | 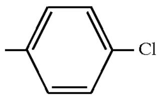 | $CHF_2$ | |
| 354 | 2 | $CH(CH_3)_2$ | $OCH(CH_3)_2$ | $CHF_2$ | |
| 355 | 2 | $CH(CH_3)_2$ | 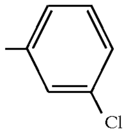 | $CHF_2$ | |
| 356 | 2 | $CH(CH_3)_2$ | 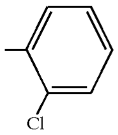 | $CHF_2$ | |

TABLE 2-continued
Examples of the compounds of the formula (I)
| Ex. No. | n | $R^1$ | $R^2$ (or 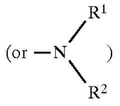) | $R^3$ | Physical data |
|---|---|---|---|---|---|
| 357 | 2 | $CH(CH_3)_2$ | 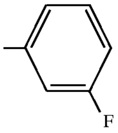 | $CHF_2$ | |
| 358 | 2 | $CH(CH_3)_2$ | 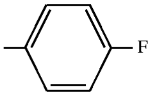 | $CHF_2$ | |
| 359 | 2 | $CH(CH_3)_2$ | 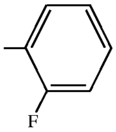 | $CHF_2$ | |
| 360 | 2 | $CH(CH_3)_2$ | 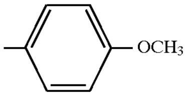 | $CHF_2$ | |
| 361 | 2 | $CH(CH_3)_2$ | 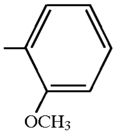 | $CHF_2$ | |
| 362 | 2 | $CH(CH_3)_2$ | 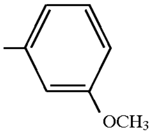 | $CHF_2$ | |
| 363 | 2 | $CH(CH_3)_2$ | 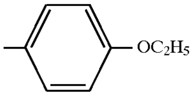 | $CHF_2$ | |
| 364 | 2 | $CH(CH_3)_2$ | 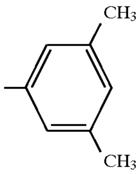 | $CHF_2$ | |
| 365 | 2 | $CH(CH_3)_2$ | 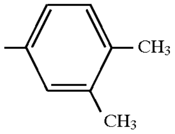 | $CHF_2$ | |
| 366 | 2 | $CH(CH_3)_2$ | 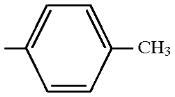 | $CHF_2$ | |

TABLE 2-continued
Examples of the compounds of the formula (I)
| Ex. No. | n | $R^1$ | $R^2$ 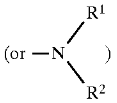 | $R^3$ | Physical data |
|---|---|---|---|---|---|
| 367 | 2 | $CH(CH_3)_2$ | 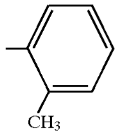 | $CHF_2$ | |
| 368 | 2 | $CH(CH_3)_2$ | 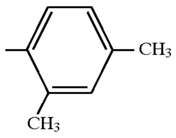 | $CHF_2$ | |
| 369 | 2 | $CH_3$ | 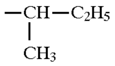 | $CHF_2$ | |
| 370 | 2 | $CH_3$ | 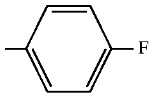 | $CHF_2$ | |
| 371 | 2 | $C_2H_5$ | 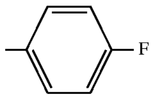 | $CHF_2$ | |
| 372 | 2 | $CH_3$ | 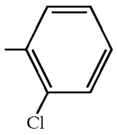 | $CHF_2$ | |
| 373 | 2 | $C_2H_5$ | 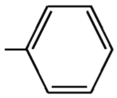 | $CHF_2$ | |
| 374 | 2 | $CH_3$ | 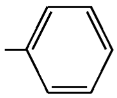 | $CHF_2$ | |
| 375 | 2 | n-$C_3H_7$ | n-$C_3H_7$ | $CHF_2$ | |
| 376 | 2 | 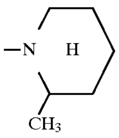 | | $CHF_2$ | |
| 377 | 2 | 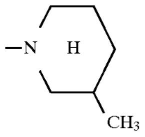 | | $CHF_2$ | |
| 378 | 2 | 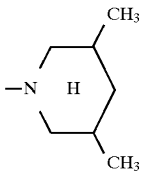 | | $CHF_2$ | |

TABLE 2-continued

Examples of the compounds of the formula (I)

| Ex. No. | n | $R^1$ | (or 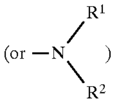) | $R^2$ | $R^3$ | Physical data |
|---|---|---|---|---|---|---|
| 379 | 2 | $CH_3$ | | $n-C_4H_9$ | $CHF_2$ | |
| 380 | 2 | | 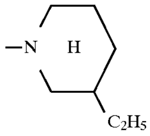 | | $CHF_2$ | |
| 381 | 2 | $CH_2-CH=CH_2$ | | $CH_2-CH=CH_2$ | $CHF_2$ | |

Starting compounds of the formula (II):

Example (II-1)

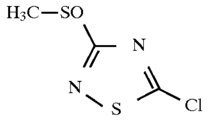

148 g (0.73 mol) of 5-chloro-3-methylthio-1,2,4-thiadiazole are dissolved in a mixture comprising 500 ml of methanol and 23 g of concentrated sulphuric acid, and the whole is heated to reflux. 90.6 g (0.8 mol of $H_2O_2$) of a 30% aqueous solution of hydrogen peroxide are then added dropwise. The reaction mixture is heated under reflux for 3 hours. It is then concentrated and the residue is shaken with chloroform/water; the organic phase is washed with sodium hydrogen carbonate solution and then with water, dried with sodium sulphate and filtered. The solvent is carefully distilled off from the filtrate under a water pump vacuum.

113 g (85% of theory) of 5-chloro-3-methylsulphinyl-1,2,4-thiadiazole are obtained as a crystalline product with a melting point of 72° C.

The following compounds, for example, may be prepared in analogy with example (II-1):

3-ethylsulphinyl-, 3-n-propyl-sulphinyl-, 3-i-propyl-sulphinyl, 3-n-butyl-sulphinyl-, 3-i-butyl-sulphinyl-, 3-s-butyl-sulphinyl-, 3-benzyl-sulphinyl, 3-(2-chloro-benzyl)-sulphinyl-, 3-(3-chloro-benzyl)-sulphinyl-, 3-(4-chloro-benzyl)-sulphinyl-, 3-(3-trifluoromethyl-benzyl)-sulphinyl and 3-(4-trifluoromethyl-benzyl)-sulphinyl-5-chloro- 1,2,4-thiadiazole.

Example (II-2)

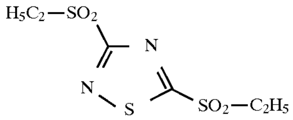

105 g (0.5 mol) of 2,5-bis-ethylthio-1,2,4-thiadiazole and 3.5 g of sodium tungstate are initially introduced into 260 ml of acetic acid, and 475 ml (5.5 mol of $H_2O_2$) of a 30% aqueous solution of hydrogen peroxide are added dropwise at 20° C. to 30° C. and within the space of approx. 90 minutes. The reaction mixture is stirred at 20° C. for 5 hours and then slowly diluted with 2.5 litres of water. The product, which has resulted in crystalline form during this procedure, is isolated by filtering it off with suction.

100 g (74% of theory) of 2,5-bis-ethylsulphonyl-1,2,4-thiadiazole are obtained with a melting point of 42° C.

The compounds of the formula (II) which are listed in the following Table 3 may also, for example, be prepared in analogy with Example (II-2).

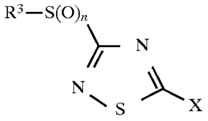

(II)

TABLE 3

Examples of the compounds of the formula (II)

| Ex. No. | n | $R^3$ | X | Melting point (°C.) |
|---|---|---|---|---|
| II-3 | 2 | $n-C_3H_7$ | $-SO_2-C_3H_7-n$ | 50 |
| II-4 | 2 | $n-C_4H_9$ | $-SO_2-C_4H_9-n$ | ($n_D^{20}$ = 1.5020) |
| II-5 | 2 | $-CH_2CH_2-O-C_2H_5$ | $-SO_2-CH_2CH_2OC_2H_5$ | 80 |
| II-6 | 2 | $-CH_2CH(CH_3)_2$ | $-SO_2-CH_2CH(CH_3)_2$ | 93 |
| II-7 | 2 | 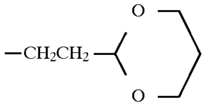 | 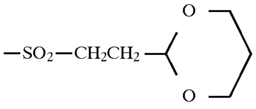 | ($n_D^{20}$ = 1.4816) |

TABLE 3-continued

Examples of the compounds of the formula (II)

| Ex. No. | n | $R^3$ | X | Melting point (°C.) |
|---|---|---|---|---|
| II-8 | 2 | 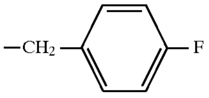 | 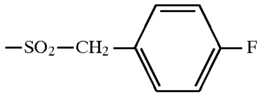 | 150 |
| II-9 | 2 | $i-C_3H_7$ | $-SO_2-C_3H_7-i$ | ($n_D^{20}$ = 1.5147) |

Application Example:

In the application example which is given below, the following compound is taken for comparison:

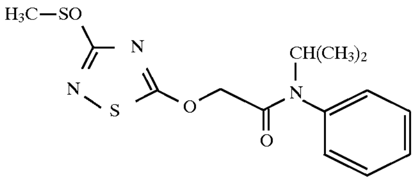

(A)

(disclosed in EP-A 348737/LeA 26031, cf. Example 28).

Example A: Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is watered with the preparation of the active compound. In this context, it is expedient to keep the amount of water per unit area constant. The concentration of the active compound in the preparation is of no importance, only the amount of active compound applied per unit area being decisive. After three weeks, the degree of damage to the plants is rated in % damage in comparison to the development of the untreated control. The figures denote:

0%=no effect (like the untreated control)

100%=total distraction

In this test, the compounds according to Preparation Examples 1, 5, 6, 7, 8, 9, 11, 12, 14, 17, 19, 20, 21, 22, 23, 24, 25, 26, 27, 28, 29, 30, 31, 32, 33, 34, 35, 36, 37, 38, 39, 41 and 42, for example, display a substantially more powerful effect against weeds than does the known compound (A) (cf. Table A) while being very well tolerated by cultivated plants, for example soya bean.

Additional novel active compounds and their rates of application, and the test plants used and the test results, are shown in the following Table B; the example numbers in this table also refer to the above preparation examples given in Table 2.

TABLE A

Pre-emergence Test/Greenhouse

| Active compound | Rate of application (g/ha) | Cotton | Lolium | Panicum | Poa | Galinsoga |
|---|---|---|---|---|---|---|
| 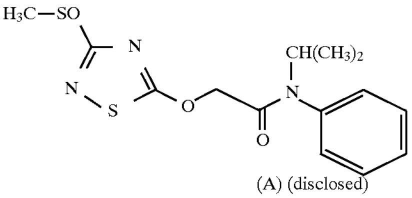 (A) (disclosed) | 250 | 0 | 20 | 0 | 50 | 20 |
| 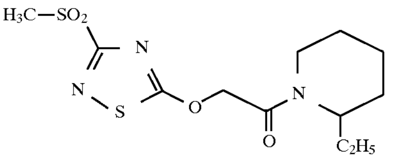 (1) | 250 | 0 | 90 | 95 | 95 | 95 |

TABLE A-continued
Pre-emergence Test/Greenhouse
| Active compound | Rate of application (g/ha) | Cotton | Lolium | Panicum | Poa | Galinsoga |
|---|---|---|---|---|---|---|
| 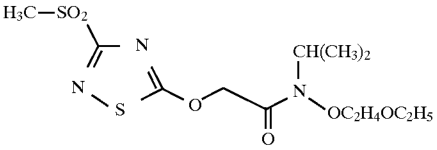 (5) | 250 | 0 | 80 | 95 | 90 | 100 |
| 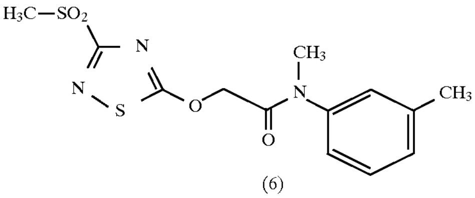 (6) | 250 | 0 | 70 | 80 | 80 | 100 |
| 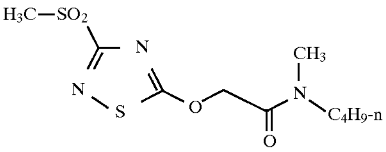 (7) | 250 | 0 | 50 | 90 | 80 | 100 |
| 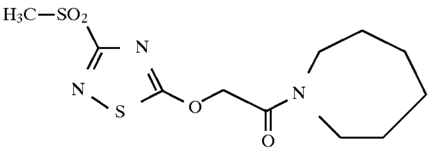 (8) | 250 | 0 | 40 | 90 | 70 | 100 |
| 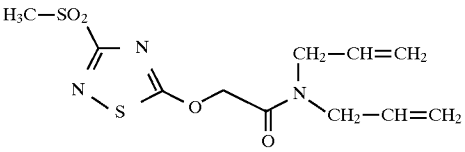 (9) | 250 | 0 | 95 | 100 | 95 | 95 |
| 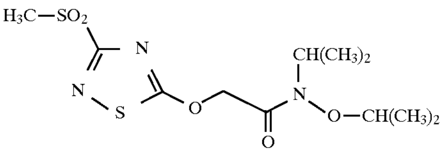 (11) | 250 | 0 | 95 | 90 | 95 | 100 |
| 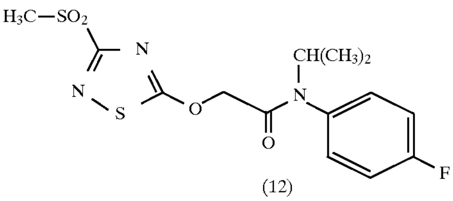 (12) | 250 | 0 | 70 | 30 | 70 | 100 |

TABLE A-continued
Pre-emergence Test/Greenhouse
| Active compound | Rate of application (g/ha) | Cotton | Lolium | Panicum | Poa | Galinsoga |
|---|---|---|---|---|---|---|
| 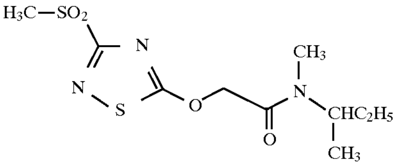 (14) | 250 | 0 | 95 | 90 | 70 | 100 |
| 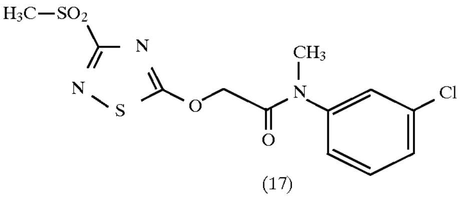 (17) | 250 | 0 | 90 | 90 | 95 | 100 |
| 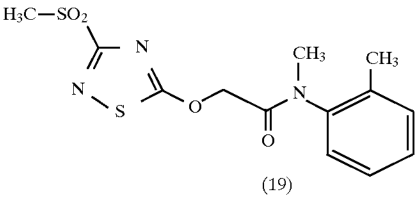 (19) | 250 | 10 | 70 | 95 | 80 | 100 |
| 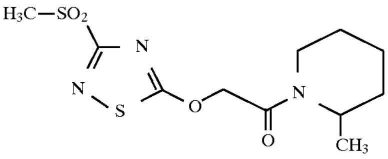 (20) | 250 | 40 | 70 | 95 | 95 | 100 |
| 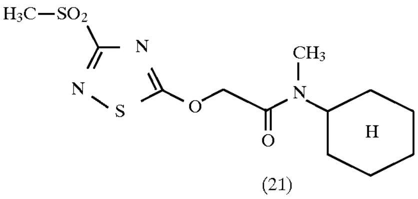 (21) | 250 | 20 | 80 | 95 | 95 | 100 |
| 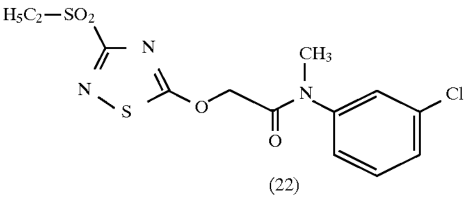 (22) | 250 | 0 | 95 | 95 | 100 | 95 |
| 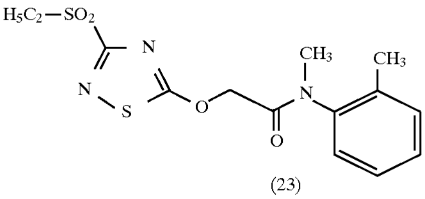 (23) | 250 | 0 | 80 | 95 | 100 | 95 |

TABLE A-continued
Pre-emergence Test/Greenhouse
| Active compound | Rate of application (g/ha) | Cotton | Lolium | Panicum | Poa | Galinsoga |
|---|---|---|---|---|---|---|
| 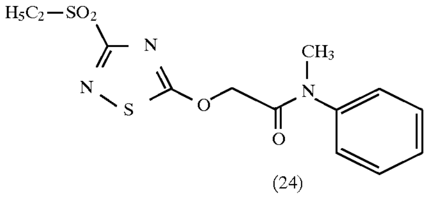 (24) | 250 | 20 | 95 | 95 | 100 | 95 |
| 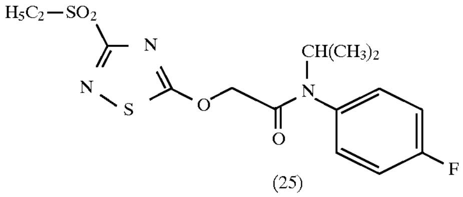 (25) | 250 | 0 | 95 | 90 | 100 | 95 |
| 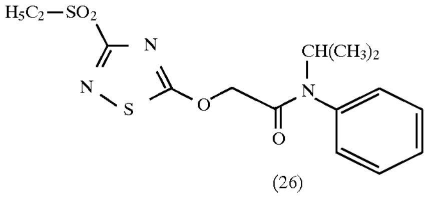 (26) | 250 | 0 | 95 | 90 | 95 | 95 |
| 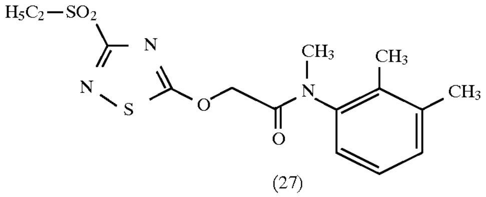 (27) | 250 | 0 | 95 | 90 | 100 | 95 |
| 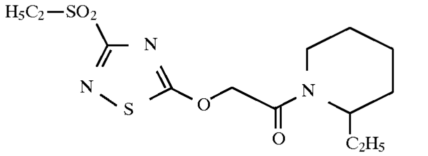 (28) | 250 | 20 | 95 | 95 | 100 | 95 |
| 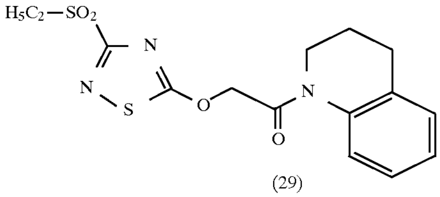 (29) | 250 | 0 | 40 | 90 | 90 | 95 |
| 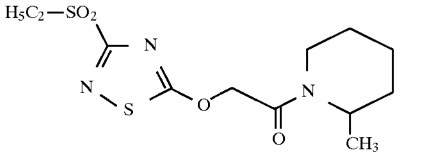 (30) | 250 | 20 | 95 | 95 | 95 | 95 |

TABLE A-continued
Pre-emergence Test/Greenhouse
| Active compound | Rate of application (g/ha) | Cotton | Lolium | Panicum | Poa | Galinsoga |
|---|---|---|---|---|---|---|
| 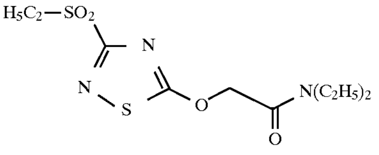 (31) | 250 | 0 | 95 | 95 | 95 | 95 |
| 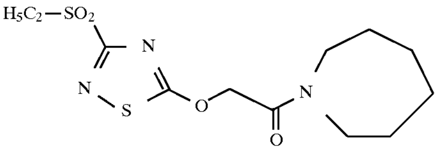 (32) | 250 | 0 | 90 | 95 | 95 | 100 |
| 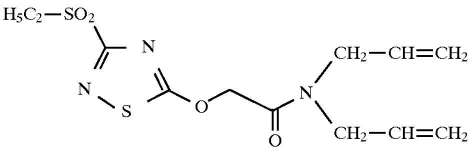 (33) | 250 | 0 | 95 | 95 | 100 | 95 |
| 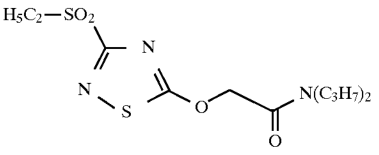 (34) | 250 | 0 | 90 | 95 | 100 | 100 |
| 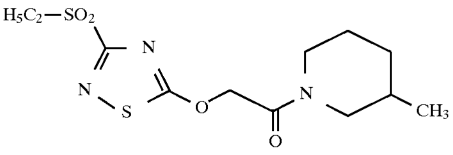 (35) | 250 | 0 | 40 | 95 | 95 | 95 |
| 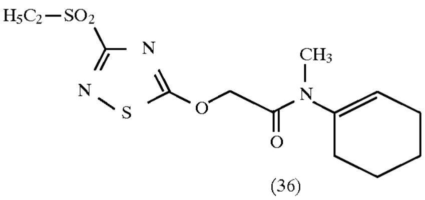 (36) | 250 | 20 | 50 | 95 | 95 | 95 |
| 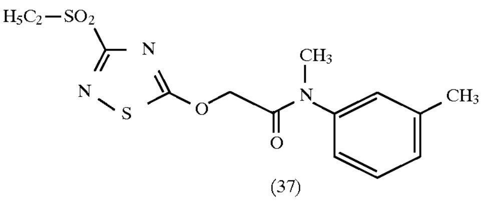 (37) | 250 | 0 | 95 | 95 | 100 | 100 |

TABLE A-continued
| Pre-emergence Test/Greenhouse | | | | | | |
|---|---|---|---|---|---|---|
| Active compound | Rate of application (g/ha) | Cotton | Lolium | Panicum | Poa | Galinsoga |
| 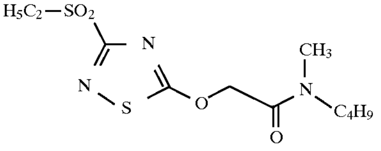 (38) | 250 | 0 | 70 | 95 | 95 | 95 |
| 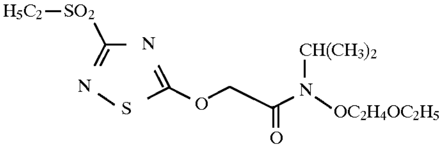 (39) | 250 | 0 | 95 | 95 | 95 | 100 |
| 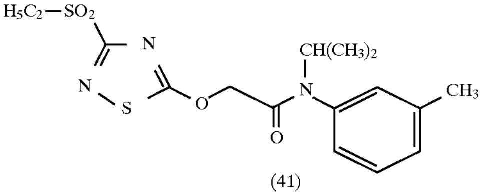 (41) | 250 | 0 | 100 | 90 | 95 | 90 |
| 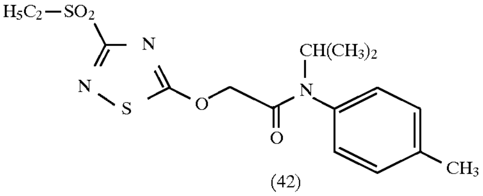 (42) | 250 | 0 | 95 | 50 | 95 | 50 |
TABLE B
| Pre-emergence Test/Greenhouse | | | | | | | | |
|---|---|---|---|---|---|---|---|---|
| Active compound No. | Rate of application (kg/ha) | Digitaria | Echinochloa | Poa | Setaria | Amaranthus | Galinsoga | Portulaca |
| 2 | 500 | 100 | 100 | 100 | 100 | 100 | — | 100 |
| 46 | 500 | 95 | 80 | 80 | 90 | 100 | 70 | — |
| 49 | 250 | 100 | 80 | 80 | 100 | 80 | 95 | 100 |
| 1 | 500 | 100 | 100 | 95 | 100 | 100 | 100 | 100 |
| 5 | 500 | 95 | 100 | 100 | 100 | 100 | 100 | 100 |
| 6 | 500 | 100 | 100 | 95 | 100 | 100 | 100 | 100 |
| 7 | 500 | 95 | 100 | 95 | 95 | 80 | 100 | 95 |
| 8 | 500 | 100 | 100 | 95 | 90 | 90 | 100 | 100 |
| 9 | 500 | 95 | 100 | 80 | 100 | 50 | 100 | 100 |
| 11 | 500 | 95 | 100 | 95 | 100 | 95 | 100 | 95 |
| 12 | 500 | 95 | 100 | 80 | 95 | — | 100 | — |
| 19 | 250 | 95 | 95 | 80 | 95 | — | 100 | 70 |
| 14 | 500 | 95 | 100 | 90 | 100 | 100 | 100 | 100 |
| 16 | 500 | 95 | 95 | 80 | 70 | 80 | 100 | 100 |
| 17 | 500 | 100 | 80 | 95 | 95 | 95 | 100 | 95 |
| 20 | 250 | 95 | 95 | 95 | 95 | 95 | 100 | 80 |
| 21 | 250 | 95 | 95 | 80 | 95 | 80 | 100 | — |
| 22 | 500 | 95 | 95 | 100 | 95 | 80 | 95 | 100 |
| 23 | 500 | 100 | 100 | 100 | 95 | 70 | 95 | 100 |
| 24 | 500 | 100 | 100 | 100 | 100 | 100 | 95 | 100 |
| 25 | 500 | 95 | 100 | 100 | 95 | — | 95 | — |
| 26 | 500 | 95 | 100 | 100 | 95 | — | 95 | — |
| 27 | 500 | 95 | 95 | 100 | 95 | 70 | 95 | 95 |

TABLE B-continued
| Active compound No. | Rate of application (kg/ha) | Pre-emergence Test/Greenhouse Digitaria | Echinochloa | Poa | Setaria | Amaranthus | Galinsoga | Portulaca |
|---|---|---|---|---|---|---|---|---|
| 28 | 500 | 100 | 100 | 100 | 100 | 70 | 95 | 100 |
| 29 | 500 | 95 | 95 | 90 | 90 | 70 | 95 | 95 |
| 30 | 500 | 100 | 95 | 100 | 100 | 80 | 95 | 100 |
| 31 | 500 | 100 | 100 | 100 | 100 | 70 | 95 | 100 |
| 32 | 500 | 100 | 95 | 95 | 100 | 70 | 100 | 100 |
| 33 | 500 | 100 | 100 | 100 | 100 | 100 | 95 | 100 |
| 34 | 500 | 100 | 100 | 100 | 95 | 95 | 100 | 100 |
| 35 | 500 | 100 | 100 | 100 | 100 | 95 | 100 | 90 |
| 36 | 500 | 100 | 100 | 95 | 100 | 95 | 95 | 100 |
| 37 | 500 | 100 | 100 | 100 | 100 | 90 | 100 | 100 |
| 38 | 500 | 100 | 100 | 100 | 100 | 95 | 95 | 100 |
| 39 | 500 | 100 | 100 | 100 | 100 | 95 | 100 | 100 |
| 40 | 500 | 95 | 95 | 95 | 95 | — | — | — |
| 41 | 500 | 100 | 100 | 95 | 100 | — | 90 | — |
| 42 | 500 | 95 | 100 | 100 | 95 | — | 95 | — |
| 190 | 250 | 100 | 100 | 100 | 95 | 95 | 95 | 95 |
| 191 | 250 | 95 | 100 | 95 | 95 | 80 | 80 | 60 |
| 194 | 500 | 100 | 95 | 100 | 100 | 100 | 95 | 100 |
| 196 | 250 | 95 | 100 | 100 | 100 | 95 | 100 | 95 |
| 53 | 250 | 95 | 100 | 95 | 95 | — | 95 | 70 |
| 198 | 250 | 100 | 100 | 100 | 95 | 90 | 100 | 95 |
| 199 | 250 | 95 | 100 | 100 | 100 | 60 | 95 | 95 |
| 55 | 250 | 95 | 100 | 100 | 100 | 100 | 90 | 95 |
| 56 | 250 | 100 | 100 | 100 | 100 | 100 | 95 | 95 |
| 57 | 250 | 100 | 100 | 100 | 100 | 100 | 100 | 100 |
| 58 | 250 | 100 | 100 | 100 | 100 | 100 | 95 | 90 |
| 201 | 250 | 100 | 100 | 100 | 100 | 95 | 95 | 60 |
| 203 | 250 | 100 | 100 | 100 | 95 | 100 | 95 | 90 |
| 75 | 500 | 100 | 95 | 100 | 100 | 70 | 95 | 95 |
| 207 | 500 | 100 | 100 | 100 | 95 | 100 | 95 | 100 |
| 208 | 500 | 95 | 100 | 100 | 100 | 100 | 95 | 100 |
| 78 | 500 | 100 | 100 | 100 | 100 | 100 | 100 | 100 |
| 79 | 500 | 100 | 100 | 100 | 100 | 100 | 100 | 100 |
| 80 | 500 | 100 | 100 | 100 | 100 | 100 | 100 | 100 |
| 87 | 500 | 95 | 50 | 95 | 95 | 80 | 100 | 95 |
| 210 | 500 | 95 | 100 | 95 | 100 | 100 | 100 | 95 |
| 212 | 500 | 95 | 60 | 95 | 95 | 100 | 100 | 100 |
| 213 | 500 | 95 | 90 | 95 | 95 | 100 | 95 | 50 |
| 310 | 250 | 100 | 100 | 95 | 95 | 100 | 95 | 95 |
| 216 | 250 | 95 | 95 | 100 | 100 | 95 | 100 | 100 |
| 219 | 250 | 100 | 100 | 100 | 95 | — | 100 | 100 |
| 220 | 250 | 100 | 100 | 100 | 100 | 100 | 100 | 100 |
| 221 | 250 | 95 | 95 | 100 | 100 | 60 | 100 | 95 |
| 103 | 250 | 100 | 100 | 100 | 100 | 50 | 100 | 100 |
| 116 | 250 | 95 | 95 | 100 | 100 | — | 90 | — |
| 222 | 250 | 95 | 100 | 100 | 95 | — | 100 | 70 |
| 225 | 250 | 100 | 100 | 100 | 100 | 100 | 100 | 100 |
| 226 | 250 | 95 | 80 | 100 | 100 | 100 | 100 | 100 |
| 227 | 250 | 100 | 70 | 100 | 95 | 100 | 100 | 100 |
| 228 | 250 | 100 | 100 | 100 | 100 | 100 | 95 | 100 |
| 229 | 250 | 100 | 90 | 80 | 95 | — | 95 | 60 |
| 230 | 250 | 95 | 95 | 100 | 95 | 95 | 60 | — |
| 235 | 250 | 100 | 95 | 100 | 95 | 95 | 95 | 95 |
| 236 | 250 | 95 | 80 | 90 | 90 | — | — | — |
| 237 | 250 | 95 | 95 | 100 | 95 | 95 | 95 | 60 |
| 240 | 250 | 100 | 95 | 100 | 100 | 90 | 95 | 95 |
| 243 | 500 | 100 | — | 100 | 95 | 100 | 100 | 100 |
| 247 | 250 | 100 | 100 | 100 | 100 | 100 | 95 | 100 |
| 251 | 250 | 100 | 95 | 100 | 90 | 100 | 100 | 95 |
We claim:
1. An alkylsulphinyl- or alkylsulphonyl-1,2,4-thiadiazolyloxyacetamide of the formula
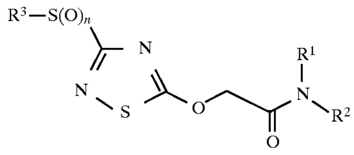
(I)

in which n represents the numbers 1 or 2, $R^1$ represents hydrogen or $C_1$–$C_8$-alkyl (which is optionally substituted by fluorine, chlorine, cyano or $C_1$–$C_4$-alkoxy), represents $C_2$–$C_8$-alkenyl (which is optionally substituted by fluorine and/or chlorine), represents $C_2$–$C_8$-alkinyl or represents benzyl, $R^2$ represents $C_1$–$C_8$-alkyl optionally substituted by fluorine chlorine, cyano or $C_1$–$C_4$-alkoxy, or $C_2$–$C_8$-alkenyl optionally substituted by fluorine or chlorine, represents $C_2$–$C_8$-alkinyl, represents $C_3$–$C_6$-cycloalkyl optionally substituted by chlorine or $C_1$–$C_3$-alkyl, represents $C_5$- or $C_6$-cycloalkenyl, represents benzyl optionally substituted by fluorine, chlorine or $C_1$–$C_4$-alkyl, represents $C_1$–$C_8$-alkoxy optionally substituted by $C_1$–$C_4$-alkoxy, or represents $C_3$–$C_4$-alkenyloxy, or $R^1$ and $R^2$, together with the nitrogen atom to which they are bonded, form a saturated or unsaturated, five- to seven-membered nitrogen heterocycle which is optionally substituted once to three times by $C_1$–$C_3$-alkyl and which is optionally benzo fused, and $R^3$ represents $C_2$–$C_4$-alkyl optionally substituted by fluorine, chlorine, bromine, cyano, $C_1$–$C_4$-alkoxy, dioxolanyl or dioxanyl or represents phenyl or phenyl-$C_1$–$C_2$-alkyl which are in each case optionally substituted by fluorine, chlorine, bromine, cyano, nitro, $C_1$–$C_4$-alkyl or $C_1$–$C_4$-alkoxy.

2. An alkylsulphinyl- or alkylsulphonyl-1,2,4-thiadiazolyloxyacetamide according to claim 1, in which n represents the numbers 1 or 2, $R^1$ represents methyl, ethyl, n- or i-propyl, n-, i- or s-butyl, or n-, i- or s-pentyl which are in each case optionally substituted by fluorine, chlorine, cyano, methoxy or ethoxy, or represents propenyl, butenyl, propinyl or butinyl, $R^2$ represents methyl, ethyl, n- or i-propyl, n-, i or s-butyl, n-, i- or s-pentyl, or n-, i- or s-hexyl which are in each case optionally substituted by fluorine, chlorine, cyano, methoxy or ethoxy, represents propenyl, butenyl, pentenyl, propinyl, butinyl or pentinyl, represents cyclopentyl or cyclohexyl which are in each case optionally substituted by methyl or ethyl, represents cyclohexenyl, represents benzyl which is optionally substituted by fluorine, chlorine or methyl, or represents methoxy, ethoxy, n- or i-propoxy, n-, i- or s-butoxy, or n-, i- or s-pentyloxy which are in each case optionally substituted by methoxy or ethoxy, or $R^1$ and $R^2$, together with the nitrogen atom to which they are bonded, represent piperidinyl which is optionally substituted one to three times by methyl and/or ethyl, represent pyrrolidinyl which is optionally substituted once or twice by methyl or ethyl, represent perhydroazepinyl or represent 1,2,3,4-tetrahydro(iso) quinolinyl, and $R^3$ represents ethyl, n- or i-propyl, n-, i-, s- or t-butyl, n-, i-, s- or t-pentyl which are in each case optionally substituted by fluorine, chlorine, -cyano, methoxy or ethoxy or represents phenyl or benzyl which are in each case optionally substituted by fluorine, chlorine, cyano, methyl or methoxy.

3. A herbicidal composition which comprises an effective amount of a compound according to claim 1 and an inert carrier.

4. A process for controlling weeds which comprises applying a compound according to claim 1 to said weeds or to a habitat in which they reside.

5. A process for preparing alkylsulphinyl- and alkylsulphonyl-1,2,4-thiadiazolyloxyacetamides of the formula (I) according to claim 1, which comprises reacting (a) 1,2,4-thiadiazole derivatives of the general formula (II)

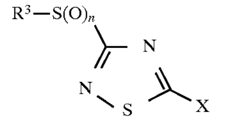

(II)

in which

X represents halogen or the grouping —$S(O)_n$—$R^3$, and n and $R^3$ have the meaning given in claim 1, with hydroxyacetamides of the general formula (III)

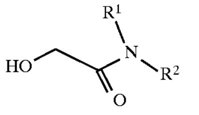

(III)

in which $R^1$ and $R^2$ have the meaning given in claim 1, where appropriate in the presence of a diluent, where appropriate in the presence of an acid-binding agent and where appropriate in the presence of a catalyst, or in that (b) alkyl(aryl-, aralkyl-)thio-1,2,4-thiadiazolyloxyacetamides of the general formula (IV)

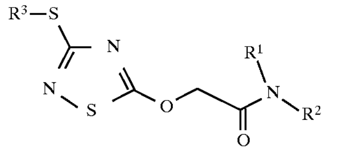

(IV)

in which $R^1$, $R^2$ and $R^3$ have the meaning given in claim 1, are reacted with an oxidizing agent, where appropriate in the presence of a catalyst and where appropriate in the presence of a diluent.

6. A 1,2,4-thiadiazole derivative of the formula

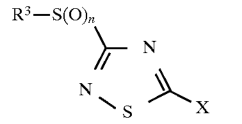

(II)

in which

X represents halogen or the grouping —$S(O)_n$—$R^3$, n represents the numbers 1 or 2, and $R^3$ represents $C_2$–$C_8$-alkyl optionally substituted by fluorine, chlorine, bromine, cyano, $C_1$–$C_4$-alkoxy, dioxolanyl or dioxanyl or represents phenyl-$C_1$–$C_2$-alkyl optionally substituted by fluorine, chlorine, bromine, cyano, nitro, $C_1$–$C_4$-alkyl or $C_1$–$C_4$-alkoxy.

* * * * *

UNITED STATES PATENT AND TRADEMARK OFFICE
CERTIFICATE OF CORRECTION

PATENT NO : 5,827,800
DATED : October 27,1998
INVENTOR(S) : Heinz Forster, et al.

It is certified that error appears in the above-identified patent and that said Letters Patent is hereby corrected as shown below:

Title Page, "PCT Pub. No." Delete "WO95/29990" and substitute -- WO95/29905--

Signed and Sealed this

Twenty-fourth Day of August, 1999

Attest:

Q. TODD DICKINSON

Attesting Officer

*Acting Commissioner of Patents and Trademarks*